United States Patent
Brophy et al.

(10) Patent No.: US 10,531,654 B2
(45) Date of Patent: Jan. 14, 2020

(54) METHODS AND COMPOSITIONS FOR VEIN HARVEST AND AUTOGRAFTING

(71) Applicants: Vanderbilt University, Nashville, TN (US); The United States Government as Represented by the Department of Veterans Affairs, Washington, DC (US)

(72) Inventors: Colleen M. Brophy, Nashville, TN (US); Padmini Komalavilas, Nashville, TN (US); Joyce Cheung-Flynn, Nashville, TN (US); Kyle M Hocking, Nashville, TN (US); Susan S Eagle, Nashville, TN (US)

(73) Assignees: VANDERBILT UNIVERSITY, Nashville, TN (US); THE UNITED STATES GOVERNMENT AS REPRESENTED BY THE DEPARTMENT OF VETERANS AFFAIRS, Washington, DC (US)

( * ) Notice: Subject to any disclaimer, the term of this patent is extended or adjusted under 35 U.S.C. 154(b) by 423 days.

(21) Appl. No.: 14/188,993

(22) Filed: Feb. 25, 2014

(65) Prior Publication Data
US 2014/0220547 A1 Aug. 7, 2014

Related U.S. Application Data

(62) Division of application No. 12/963,375, filed on Dec. 8, 2010, now Pat. No. 8,691,556.

(60) Provisional application No. 61/267,640, filed on Dec. 8, 2009.

(51) Int. Cl.
| | |
|---|---|
| *A01N 1/02* | (2006.01) |
| *A61K 31/185* | (2006.01) |
| *A61K 35/44* | (2015.01) |
| *A61M 39/06* | (2006.01) |

(52) U.S. Cl.
CPC ......... *A01N 1/0226* (2013.01); *A01N 1/0247* (2013.01); *A01N 1/0278* (2013.01); *A61K 31/185* (2013.01); *A61K 35/44* (2013.01); *A61M 39/06* (2013.01)

(58) Field of Classification Search
None
See application file for complete search history.

(56) References Cited

U.S. PATENT DOCUMENTS

| | | | |
|---|---|---|---|
| 5,746,778 A | 5/1998 | Jankewitz et al. | |
| 6,608,038 B2* | 8/2003 | Caplan | A61K 38/1709 435/320.1 |
| 6,812,226 B2 | 11/2004 | Baxter et al. | |
| 7,241,776 B2 | 7/2007 | Carroll et al. | |
| 7,326,792 B2 | 2/2008 | Shum et al. | |
| 7,709,469 B2 | 5/2010 | Carroll et al. | |
| 7,718,693 B2 | 5/2010 | Walter | |
| 7,741,493 B2 | 6/2010 | Shum et al. | |
| 8,397,713 B2* | 3/2013 | Wachter | A61M 15/0086 128/200.14 |
| 8,519,121 B2* | 8/2013 | Xie | C08B 37/0003 536/112 |
| 9,023,787 B2* | 5/2015 | Yaffe | A61K 31/00 424/649 |
| 2002/0182646 A1 | 12/2002 | Ke et al. | |
| 2005/0026916 A1 | 2/2005 | Sum et al. | |
| 2005/0054013 A1 | 3/2005 | Ke et al. | |
| 2007/0082930 A1 | 4/2007 | Boughton-Smith et al. | |
| 2007/0122849 A1 | 5/2007 | Peekhaus et al. | |
| 2007/0269256 A1 | 11/2007 | Dubinski | |
| 2008/0009541 A1 | 1/2008 | Chambers et al. | |
| 2008/0132550 A1 | 6/2008 | Shum et al. | |
| 2008/0221027 A1 | 9/2008 | Crosbie et al. | |
| 2009/0005330 A1 | 1/2009 | Jimenez et al. | |
| 2009/0149524 A1 | 6/2009 | Beswick et al. | |
| 2009/0197928 A1 | 8/2009 | Beswick et al. | |
| 2009/0215727 A1 | 8/2009 | Douglas | |
| 2009/0264501 A9 | 10/2009 | Jimenez et al. | |
| 2009/0281166 A1* | 11/2009 | Gleave | C12Q 1/6886 514/44 A |

(Continued)

FOREIGN PATENT DOCUMENTS

| | | |
|---|---|---|
| EP | 1 281 357 | 2/2003 |
| WO | WO 2005/019182 | 3/2005 |

(Continued)

OTHER PUBLICATIONS

Alcaraz et al., "Novel P2X7 receptor antagonists," *Bioorg. Med. Chem. Lett.*, 13:4043-6, 2003.
Alexander et al., "Efficacy and safety of edifoligide, an E2F transcription factor decoy, for prevention of vein graft failure following coronary artery bypass graft surgery: Prevent IV: a randomized controlled trial," *JAMA*, 294:2446-54, 2005.
Allaire and Clowes, "Endothelial cell injury in cardiovascular surgery: the intimal hyperplastic response," *Ann. Thorac. Surg.*, 63:582-91, 1997.
Cario-Toumaniantz et al., "P2X$_7$ receptor activation-induced contraction and lysis in human saphenous vein smooth muscle," *Circulation Research*, 83(2):196-203, 1998.

(Continued)

*Primary Examiner* — Michail A Belyavskyi
(74) *Attorney, Agent, or Firm* — Parker Highlander PLLC

(57) ABSTRACT

The leading cause of graft failure is the subsequent development of intimal hyperplasia, which represents a response to injury that is thought to involve smooth muscle proliferation, migration, phenotypic modulation, and extracellular matrix (ECM) deposition. Surgical techniques typically employed for vein harvest—stretching the vein, placing the vein in low pH, solutions, and the use of toxic surgical skin markers—are shown here to cause injury. The invention therefore provides for non-toxic surgical markers than also protect against stretch-induced loss of functional viability, along with other additives. Devices and compositions for reducing physical stress or protecting from the effects flowing therefrom, also are provided.

22 Claims, 20 Drawing Sheets
Specification includes a Sequence Listing.

(56) References Cited

U.S. PATENT DOCUMENTS

| | | |
|---|---|---|
| 2010/0036101 A1 | 2/2010 | Gidley-Baird et al. |
| 2010/0056595 A1 | 3/2010 | Beswick et al. |
| 2010/0075968 A1 | 3/2010 | Beswick et al. |
| 2010/0105068 A1 | 4/2010 | Barden et al. |
| 2010/0144727 A1 | 6/2010 | Beswick et al. |
| 2010/0144829 A1 | 6/2010 | Chambers et al. |
| 2010/0160373 A1 | 6/2010 | Berger et al. |
| 2010/0160384 A1 | 6/2010 | Berger et al. |
| 2010/0160387 A1 | 6/2010 | Lopez-Tapia et al. |
| 2010/0160388 A1 | 6/2010 | Brotherton-Pleiss et al. |
| 2010/0160389 A1 | 6/2010 | Berger et al. |
| 2010/0168171 A1 | 7/2010 | Beswick et al. |
| 2010/0210705 A1 | 8/2010 | Gleave et al. |
| 2010/0286390 A1 | 11/2010 | Shigeta et al. |
| 2010/0292295 A1 | 11/2010 | Steadman et al. |
| 2010/0297224 A1 | 11/2010 | Walter |
| 2013/0136725 A1* | 5/2013 | Gojon-Romanillos ................ A61K 33/04 424/94.1 |
| 2015/0079175 A1* | 3/2015 | Junior ................ A61K 31/519 424/489 |

FOREIGN PATENT DOCUMENTS

| | | |
|---|---|---|
| WO | WO 2007/002139 | 1/2007 |
| WO | WO 2007/070301 | 6/2007 |
| WO | WO 2008111010 | * 9/2008 |
| WO | WO 2009129509 | * 10/2009 |

OTHER PUBLICATIONS

Carroll et al., "Selective P2X(7) receptor antagonists for chronic inflammation and pain," *Purinergic Signal.*, 5:63-73, 2009.
Cavallari et al., "Functional and morphological evaluation of canine veins following preservation in different storage media", *Journal of Surgical Research*, 68:106-115, 1997.
Clowes and Reidy, "Prevention of stenosis after vascular reconstruction: pharmacologic control of intimal hyperplasia—a review," *J. Vasc. Surg.*, 13:885-91, 1991.
Dashwood and Loesch, "Surgical damage of the saphenous vein and graft patency," *J. Thorac. Cardiovasc. Surg.*, 133:274-5, 2007.
Dashwood et al., "Surgical trauma and vein graft failure: further evidence for a role of ET-1 in graft occlusion," *J. Cardiovasc. Pharmacol.*, 44:S16-9, 2004.
Dion et al., "A novel preservation medium protecting prostacyclin production and endothelial integrity of the human saphenous vein graft", *Thrombosis Research*, Supp. XII:81-86, 1990.
Dries et al., "The influence of harvesting technique on endothelial preservation in saphenous veins," *J Surg Res.*, 52(3):219-225, 1992.
Fulton et al., "Preservation of the endothelium in venous bypass grafts: Relevance for graft patency," *Asia Pacific Heart Journal*, 6(2):98-106, 1997.

Fulton, et al. "Preservation of the Endothelium in Venous Bypass Grafts: Relevance for Graft Patency." *The Asia Pacific Heart Journal.* vol. 6, Issue 2, Sep. 1997, pp. 98-106.
International Preliminary Report on Patentability issued in PCT/US2010/059459, dated Jun. 21, 2012.
International Search Report and Written Opinion issued in PCT/US2010/059459, dated Jul. 18, 2011.
Karabult et al., "The effects of various preparation techniques by means of cleaning solutions an applied pressures on the surface morphology of saphenous vein endothelial cells during coronary bypass surgery: a light and scanning electron microscopical study," *Proceedings of Scanning*, 21(2): 149-150, 1999.
Kent and Liu, "Intimal hyperplasia—still here after all these years!" *Ann. Vasc. Surg.*, 18:135-7, 2004.
LoGerfo et al., "Integrity of vein grafts as a function of initial intimal and medial preservation," *Circulation*, 68:11117-24, 1983.
Mann et al., "Ex-vivo gene therapy of human vascular bypass grafts with E2F decoy: the Prevent single-centre, randomised, controlled trial," *Lancet*, 354:1493-8, 1999.
Mosse et al., "Smooth muscle phenotypic expression in human carotid arteries. I. Comparison of cells from diffuse intimal thickenings adjacent to atheromatous plaques with those of the media," *Lab Invest.*, 53:556-62, 1985.
Motwani and Topol, "Aortocoronary saphenous vein graft disease: pathogenesis, predisposition, and prevention," *Circulation*, 97:916-31, 1998.
Office Action dated Jul. 31, 2013 for Application No. 201080055389.X in China.
Office Action, dated Jun. 25, 2013 for AU 2010328203.
Office Communication, issued in EP Application No. 10 807 761.1, dated Mar. 22, 2013.
Office Communication, issued in EP Application No. 10 807 761.1, dated Sep. 27, 2013.
Office Communication, issued in U.S. Appl. No. 12/963,375, dated Jan. 31, 2013.
Office Communication, issued in U.S. Appl. No. 12/963,375, dated Apr. 24, 2013.
PCT Invitation to Pay Additional Fees for International Application No. PCT/US2010/059459, dated May 25, 2011.
Peng et al., "Systemic administration of an antagonist of the ATP-sensitive receptor P2X7 improves recovery after spinal cord injury," *Proc. Natl. Acad. Sci. USA*, 106:12489-93, 2009.
Partial European Search Report issued in European Application No. 14181978.9, dated Feb. 13, 2015.
Shoemaker et al., "Evans blue and gentian violet: alternatives to methylene blue as a surgical marker dye", *The Journal of Thoracic and Cardiovascular Surgery*, 112(2): 542-4, 1996.
Stromberg, "The surgical marking pen: a comparative study", *Plast Reconstr Surg.*, 80(1):104-7, 1987.
Office Communication issued in Japanese Application No. 2015-195779, dated Oct. 24, 2016. (Translation).

* cited by examiner

FIGS. 2A-B

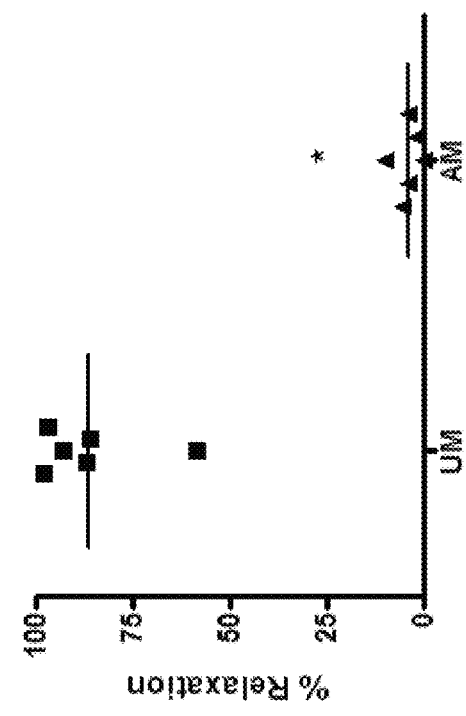
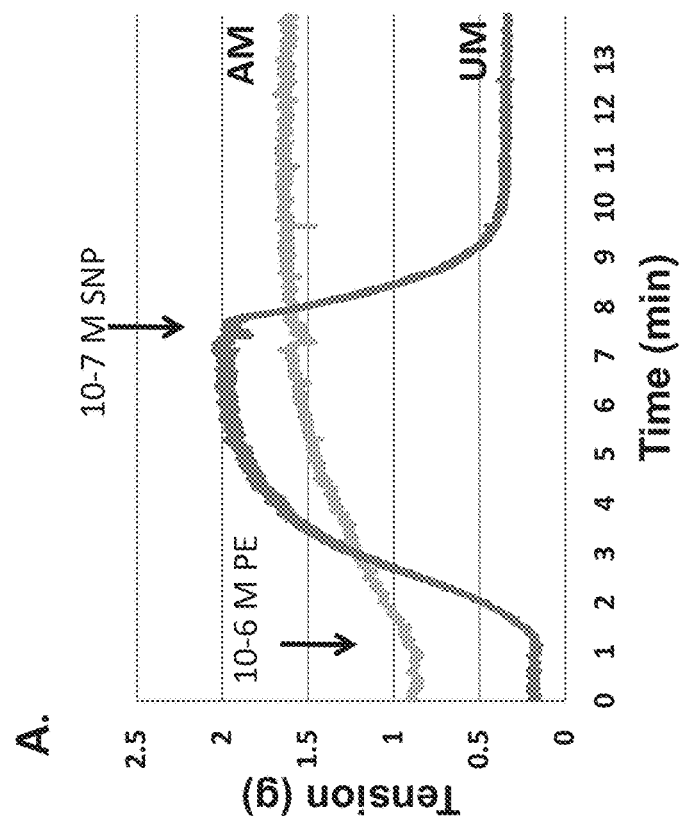
FIGS. 4A-B

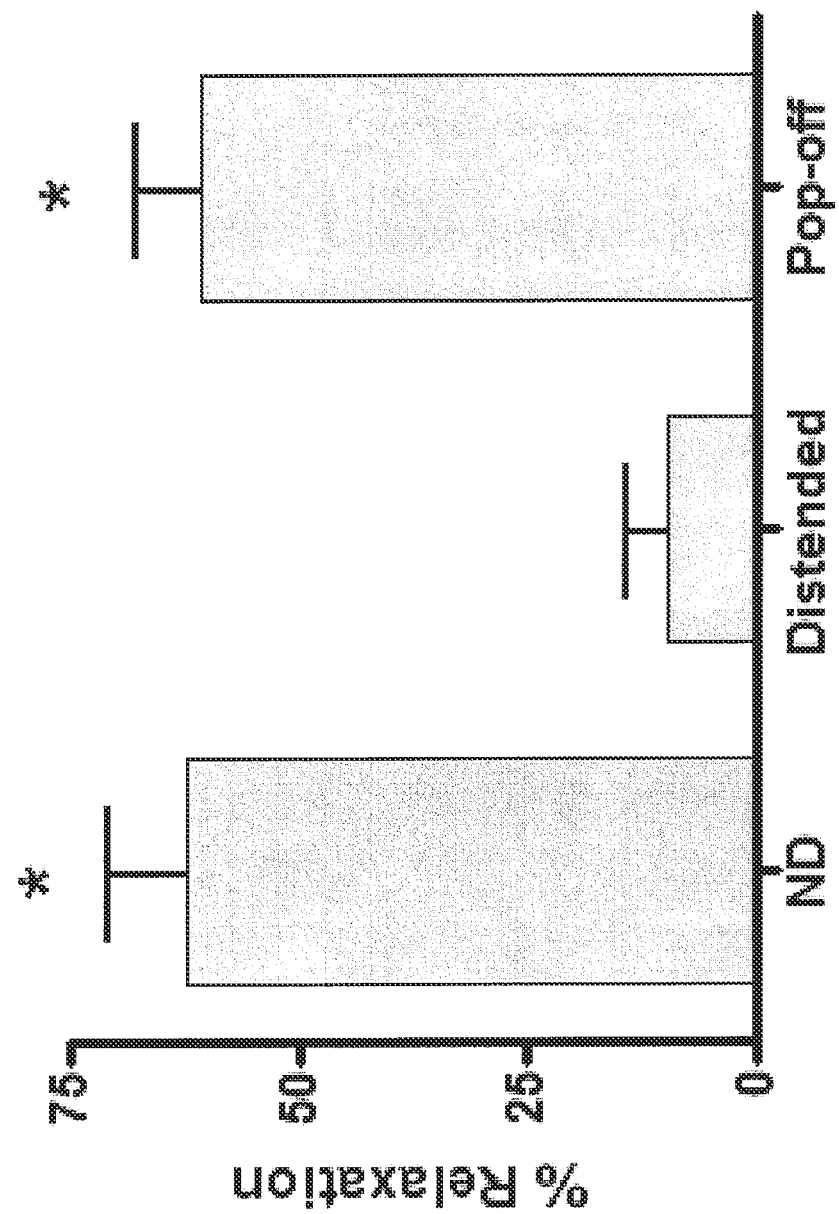

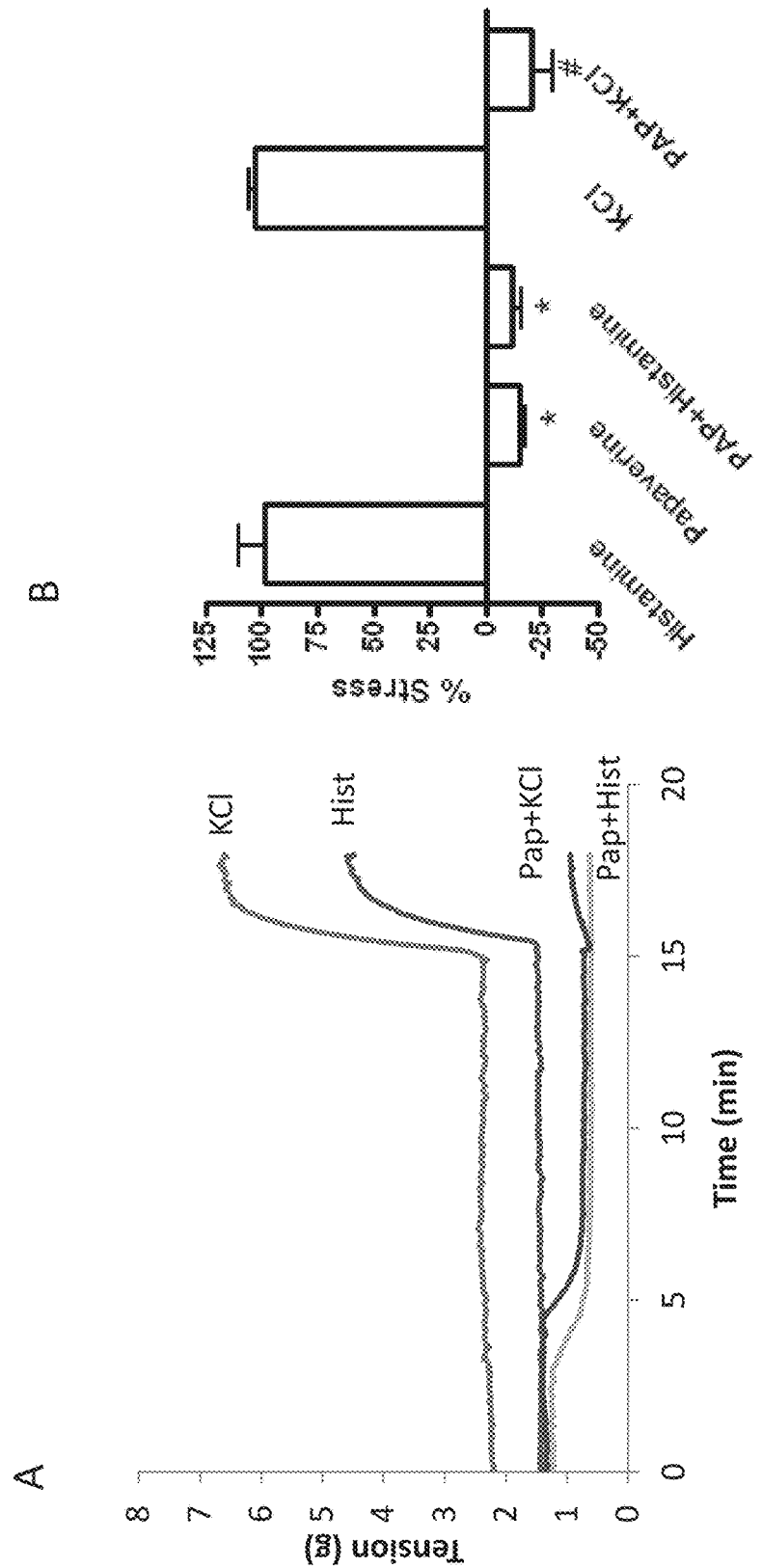
FIGS. 18A-B

FIGS. 19A-B
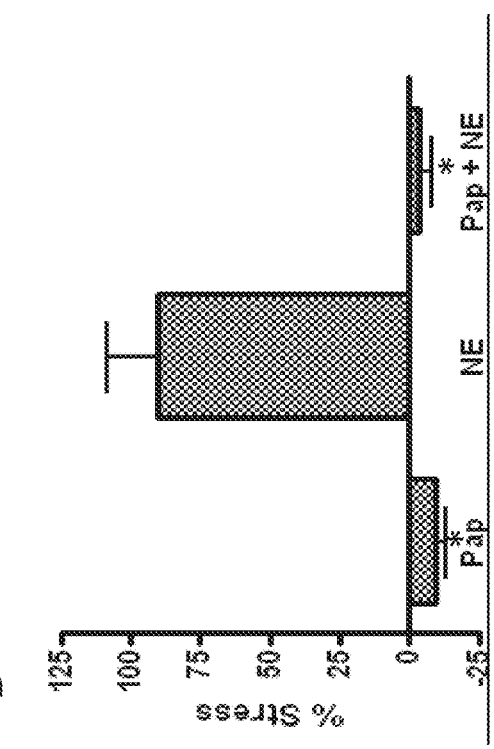
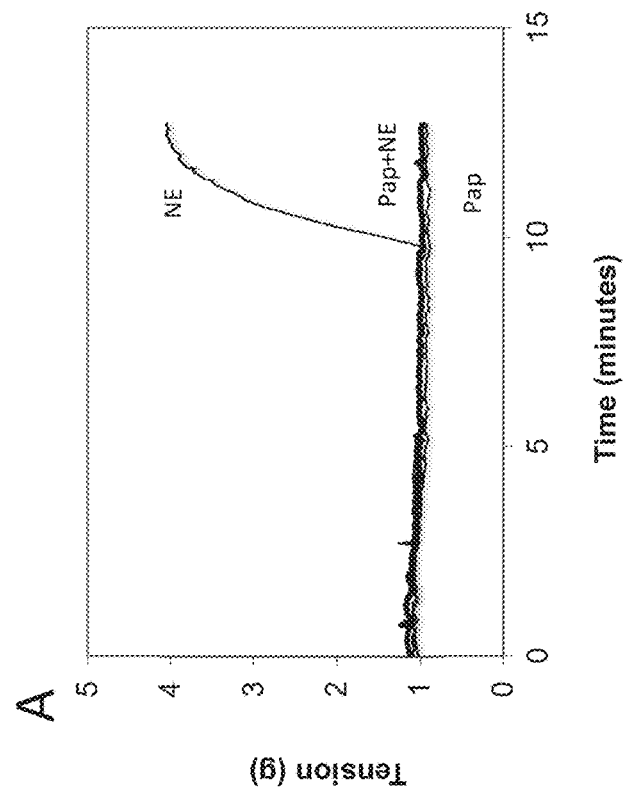

SEQUENCE LISTING

```
<160> NUMBER OF SEQ ID NOS: 5

<210> SEQ ID NO 1
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 1
gaccaaggau ggcguggugu u                                                     21

<210> SEQ ID NO 2
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 2
auacacgcug cccccggguu u                                                     21

<210> SEQ ID NO 3
<211> LENGTH: 22
<212> TYPE: RNA
<213> ORGANISM: Artificial Sequence
<220> FEATURE:
<223> OTHER INFORMATION: Synthetic oligonucleotide

<400> SEQUENCE: 3
aacucuuacu acuuaguaau cc                                                    22

<210> SEQ ID NO 4
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 4
uuguccacug accaaucugu u                                                     21

<210> SEQ ID NO 5
<211> LENGTH: 22
```

```
<212> TYPE: RNA
<213> ORGANISM: Artificial Sequence
<220> FEATURE:
<223> OTHER INFORMATION: Synthetic oligonucleotide

<400> SEQUENCE: 5
ucgcccucuc aacccagcuu uu                                          22
```

METHODS AND COMPOSITIONS FOR VEIN HARVEST AND AUTOGRAFTING

CROSS-REFERENCE TO RELATED APPLICATIONS

This application is a divisional of U.S. application Ser. No. 12/963,375, filed Dec. 8, 2010, which claims benefit of priority to U.S. Provisional Application Ser. No. 61/267,640, filed Dec. 8, 2009. The entire contents of the above-referenced disclosures are specifically incorporated herein by reference without disclaimer.

GOVERNMENT SUPPORT

The invention was made with Government support under Grant No. 2R01 HL070715 awarded by the National Institutes of Health. The Government has certain rights in the invention.

FIELD OF THE INVENTION

The invention relates generally to the fields of autologous vein, vein graft, vein preservation, tissue preservation, intimal hyperplasia, vasospasm, pharmaceuticals, devices, and vascular biology.

BACKGROUND OF THE INVENTION

Human greater saphenous vein (HSV) remains the most commonly used conduit for coronary and peripheral arterial bypass grafting. HSV is typically harvested from the leg with direct surgical exposure or endoscopic vein harvest. The branches are ligated and the vein is removed and placed on the "back table" prior to implantation. Most surgeons place the HSV in heparinized saline solution at room temperature. The vein is cannulated at the distal end and manually distended (with a syringe) with heparinized saline. This allows for identification and ligation of side branches that have been missed during harvest. This manual distension leads to injury to the vein. The veins are also marked with a surgical skin marker to optimize orientation during implantation.

Of the more than 1 million coronary bypass procedures that are undertaken each year worldwide, 10-15% of coronary vein grafts undergo early thrombotic occlusion; an additional 10-15% occlude in the next 1-5 years due to intimal hyperplasia, with a further 30-40% occluding in the subsequent 5-7 years because of progressive atherosclerosis superimposed on intimal hyperplasia. Less than half of vein grafts remain patent after 12 years (Motwani & Topol, 1998). Vein graft occlusion leads to myocardial infarction, limb loss, and death.

The leading cause of failure of arterial bypass grafts is intimal hyperplasia (Clowes & Reidy, 1991). Despite the many recent technological advances in vascular interventions, intimal hyperplasia remains an expensive, morbid, and unsolved problem. Intimal hyperplasia is mediated by a sequence of events that include vascular smooth muscle proliferation, migration, phenotypic modulation, and extra-cellular matrix production (Allaire & Clowes, 1997; Mosse et al., 1985). This process leads to pathologic narrowing of the vessel lumen, graft stenoses, and ultimately graft failure (LoGerfo et al., 1983).

A number of drugs that have been tested for their capacity to inhibit intimal hyperplasia have failed in clinical trials. Antithrombotic and antiplatelet agents such as warfarin, clopidogrel, and aspirin, have little or no effect on intimal hyperplasia (Kent & Liu, 2004). Drug eluting stents have been shown to be effective in preventing restenosis after coronary angioplasty; however, no therapeutic has been approved for autologous conduits. Two large clinical trials for the prevention of coronary and peripheral vascular vein graft failure using an E2F decoy (a short sequence of DNA that binds to transcription factors, sequestering these proteins) to prevent smooth muscle proliferation failed in their primary endpoint. Data from these large clinical trials suggests that simply limiting the proliferation response is not adequate to prevent intimal hyperplasia (Mann et al., 1999; Alexander et al., 2005). Therefore mechanisms other than proliferation need to be targeted for successful prevention of vein graft failure.

Injury to the vein graft during harvest leads to vasospasm and intimal hyperplasia, which cause the grafts to occlude. Thus, it would be of great benefit to identify new surgical methods and therapeutics to prevent injury to the graft during harvest and subsequent intimal hyperplasia.

SUMMARY OF THE INVENTION

Thus, in accordance with the present invention, there is provided a method of treating a vein explant prior to transplant comprising (a) providing a vein explant; (b) stabilizing the vein explants in a buffered solution comprising a $P2X_7$ receptor antagonist at a pH pH 7.0-7.6 to produce a stabilized vein explant; and (c) preserving functional viability of the stabilized vein explant. The method may further restore functional viability of the vein explant that before step (b) was not viable. Functional viability of smooth muscle is defined here as the ability to contract in response to depolarization or agonists. For endothelium, viability is defined the ability of pre-contracted vessels to relax in response to acetylcholine. Additionally, the buffered solution may further comprise heparin. The $P2X_7$ receptor antagonist may be erioglaucine/Blue Dye #1 or brilliant blue G, or a combination of these. Yet further, the buffered solution may comprise phosphate buffered saline, MOPS, Hepes, Pipes, acetate or Plasmalyte. The pH may be 7.35-7.45, or 7.0, 7.1, 7.2, 7.3, 7.4, 7.5 or 7.6.

Additionally, the buffered solution may further comprise magnesium sulfate or Hanks' Balanced Salt Solution.

Additionally, the buffered solution may further comprise one or more of an anti-contractile agent, an anti-oxidant agent, an oligosaccharide, a colloid agent, an anti-inflammatory agent, an endothelial function preservative, a metabolic regulator, a hydrogel, an inhibitor of heat shock protein 27 (HSP27), a regulator of HSP20, and/or an inhibitor of MAPKAP kinase 2.

Further, the anti-contractile agent may be at least one of a phosphodiesterase inhibitor (e.g., papaverine, sildenafil, tadalafil, vardenafil, udenafil, avanafil cilistizol, pentoxifylline, dipyridamole or a combination thereof), a calcium channel blocker (e.g., amlodipine, aranidipine, azelnidipine, barnidipine, cilnidipine, clevidipine, efonidipine, felodipine, lacidipine, lercanidipine, mandipine, nicardipine, nifedipine, nilvadipine, nimodipine, nisoldipine, netrendipine, prandipine or a combination thereof), a nitric oxide donor (e.g., sodium nitroprusside, nitroglycerin or a combination thereof), or a cyclic nucleotide analogue (dibutyryl cAMP, dibutyryl cGMP or a combination thereof), or a combination thereof.

Further, the anti-oxidant agent may be e.g., N-acetylcysteine, allopurinol, glutathione, mannitol, ascorbic acid, a tocopherol, a tocotrienol or a green tea phenol or a combination thereof.

Further, the oligosaccharide may be e.g., lactobionic acid, raffinose, or trehalose or a combination thereof.

Further, the colloid agent may be, e.g., hydroxyethyl starch, dextran, blood or albumin or a combination thereof.

Further, the anti-inflammatory agent may be, e.g., a corticosteroid (e.g., dexamethasone, hydrocortisone, cortisone, prednisone, prednisolone, methylprednisolone or a combination thereof), or a nonsteroidal anti-inflammatory (e.g., aspirin, ibuprophen, naproxen salicylic acid or a combination thereof), a MAPKAP kinase 2 inhibitor, anti-TNF-α, anti-IL-1-β, a Cox-2 inhibitor, or a combination thereof.

Additionally, the endothelial function preservative may be, e.g., an angiotensin converting enzyme inhibitor (e.g., enalapril, ramipril, quinapril, perindopril, lisinopril, benazepril, monopril or a combination thereof), an angiotensin receptor inhibitor (e.g. losartan), a statin (e.g. atorvastatin, cerivastatin, fluvastatin, lovastatin, mevastatin, pitavastatin, pravastatin, rosuvastatin, simvastatin or a combination thereof), metformin, aminoimidazole carboxamide ribonucleotide (AICAR) or an estrogen (e.g., estriol, estradiol, estrone, 17β-estradiol or a combination thereof).

Additionally, the metabolic regulator may be, e.g., glucose, adenosine amylin, calcitonin related gene peptide, insulin, or a combination thereof.

Additionally, the hydrogel may be composed of, for example, a natural polysaccharide such as alginate, dextran, chitosan, and glycosaminoglycan, or a hydrophilic polymer such as polyethylene glycol, methylcellulose, hydroxymethylcellulose, hydroxyethylcellulose, polyhydroxbuterate, or poly(n-isopropylacrylamide).

Further, the inhibitor of HSP27 may be, for example, an siRNA or miRNA that inhibits HSP27 expression, an anti-miRNA that enhances HSP20 expression, or a combination thereof.

Further, the inhibitor of MAPKAP kinase 2 may be, for example, a peptide inhibitor.

The explant may be marked with a non-alcohol based marker, such as, without limitation, erioglaucine/Blue Dye #1, indigotine, Allura Red AC, or brilliant blue G.

The method may further comprise flushing the lumen of the vein explant such that the internal flushing pressure does not exceed 200 mm Hg, or does not exceed 150 mm Hg.

In another embodiment, there is provided a vein transplant kit comprising (a) a tissue marking pen comprising a $P2X_7$ receptor antagonist; and (b) a physiologic buffered solution or reagents for making such. Additionally, the kit may further comprise a container suitable for bathing a vein explant. Additionally, the kit may further comprise one or more of heparin, an anti-contractile agent, an anti-oxidant agent, an oligosaccharide, a colloid agent, an anti-inflammatory agent, an endothelial function preservative, a metabolic regulator, a hydrogel, an inhibitor of a heat shock protein, magnesium sulfate, and/or an inhibitor of MAPKAP kinase 2.

The buffered solution may comprise, for example, phosphate buffered saline, MOPS, Hepes, Pipes, acetate or Plasmalyte. The buffered solution may be at pH 7.0-7.6, or at 7.35-7.45. The $P2X_7$ receptor antagonist may comprise, for example, erioglaucine/Blue Dye #1, Allura Red AC, brilliant blue G, or any combination thereof.

The kit may further comprise a device for flushing the lumen of a vein explant; said device is designed to prevent flushing pressures inside the vein explant of greater than 200 mm Hg, or greater than 150 mm Hg. The device may comprise a syringe and/or a catheter and a pop-off valve. Additionally, the syringe or catheter may comprise a bullet-shaped tip comprising a lumen for introduction into a proximal end of said vein explant. Additionally, the kit may further comprise a clamp designed to hold said vein explant.

Also provided is a device for flushing the lumen of a vein explant; said device is designed to prevent flushing pressures inside the vein explant of greater than 200 mm Hg, or greater than 150 mm Hg. The device may comprise a syringe and/or catheter and a pop-off valve. The syringe or catheter may comprise a bullet-shaped tip comprising a lumen for introduction into a distal end of said vein explant. Further, the device may further comprise a bullet-shaped plug lacking a lumen for introduction into a proximal end of said vein explant. Additionally, the device may further comprise a clamp designed to hold said vein explant.

Still yet another embodiment comprises a buffered solution of pH 7.0-7.6, wherein said buffered solution further comprises heparin and a $P2X_7$ receptor antagonist. The $P2X_7$ receptor antagonist may be, for example, erioglaucine/Blue Dye #1 or brilliant blue G, or a combination thereof. Additionally, the buffered solution may further comprise heparin, along with one or more of erioglaucine/Blue Dye #1, brilliant blue G, or both. Further, the buffered solution may comprise phosphate buffered saline, MOPS, Hepes, Pipes, acetate or Plasmalyte. Further, the pH may be 7.35-7.45, or 7.0, 7.1, 7.2, 7.3, 7.4, 7.5 or 7.6.

Additionally, the buffered solution may further comprise magnesium sulfate or Hanks' Balanced Salt Solution.

Additionally, the buffered solution may further comprises one or more of an anti-contractile agent, an anti-oxidant agent, an oligosaccharide, a colloid agent, an anti-inflammatory agent, an endothelial function preservative, a metabolic regulator, a hydrogel, an inhibitor of heat shock protein 27 (HSP27), a regulator of HSP20, an inhibitor of MAPKAP kinase 2, and/or combinations thereof.

Further, the anti-contractile agent may be a phosphodiesterase inhibitor (e.g., papaverine, sildenafil, tadalafil, vardenafil, udenafil, avanafil cilistizol, pentoxifylline, dipyridamole or a combination thereof), a calcium channel blocker (e.g. amlodipine, aranidipine, azelnidipine, barnidipine, cilnidipine, clevidipine, efonidipine, felodipine, lacidipine, lercanidipine, mandipine, nicardipine, nifedipine, nilvadipine, nimodipine, nisoldipine, netrendipine, prandipine), a nitric oxide donor (sodium nitroprusside, nitroglycerin or a combination thereof), or a cyclic nucleotide analogue (e.g. dibutyryl cAMP, dibutyryl cGMP or a combination thereof).

Further, the anti-oxidant agent may be, e.g., N-acetylcysteine, allopurinol, glutathione, mannitol, ascorbic acid, a tocopherol, a tocotrienol or a green tea phenol, or a combination thereof.

The oligosaccharide may be e.g., lactobionic acid, raffinose, trehalose, or a combination thereof.

The colloid agent may be, e.g., hydroxyethyl starch, dextran, blood or albumin or a combination thereof.

The anti-inflammatory agent may be, e.g., a corticosteroid (e.g. dexamethasone, hydrocortisone, cortisone, prednisone, prednisolone, methylprednisolone or a combination thereof), a nonsteroidal anti-inflammatory (e.g. aspirin, ibuprophen, naproxen salicylic acid or a combination thereof), a MAPKAP kinase 2 inhibitor, anti-TNF-α, anti-IL-1-β, a Cox-2 inhibitor or a combination thereof.

Further, the endothelial function preservative may be an angiotensin converting enzyme inhibitor (e.g., enalapril, ramipril, quinapril, perindopril, lisinopril, benazepril, monopril or a combination thereof), an angiotensin receptor inhibitor (e.g., losartan), a statin (e.g., atorvastatin, cerivastatin, fluvastatin, lovastatin, mevastatin, pitavastatin, pravastatin, rosuvastatin, simvastatin or a combination thereof), metformin, an estrogen (e.g., estriol, estradiol, estrone, 17β-estradiol or a combination thereof) or a combination thereof.

Further, the metabolic regulator may be e.g., glucose, adenosine amylin, calcitonin related gene peptide, insulin or a combination thereof.

Additionally, the hydrogel may be composed of a natural polysaccharide such as alginate, dextran, chitosan, and glycosaminoglycan, or a hydrophilic polymer such as polyethylene glycol, methylcellulose, hydroxymethylcellulose, hydroxyethylcellulose, polyhydroxbuterate, or poly(n-isopropylacrylamide).

Further, the inhibitor of HSP27 may be, for example, an siRNA or miRNA that inhibits HSP27 expression, an anti-miRNA that enhances HSP20 expression or a combination thereof.

The inhibitor of MAPKAP kinase 2 may be, e.g., a peptide inhibitor.

Thus, the compositions of the present invention have broad uses including use in healthcare by providing sterile medical devices and surface sterilization and decontamination.

BRIEF DESCRIPTION OF THE DRAWINGS

The following figures form part of the present specification and are included to further demonstrate certain aspects of the present invention. The invention may be better understood by reference to one or more of these figures in combination with the detailed description of specific embodiments presented herein.

FIGS. 4A-B show that the current surgical harvest techniques reduce endothelial-independent relaxation of human saphenous vein.

FIG. 17 shows that manual distension with a pressure release valve prevents loss of endothelial function in porcine saphenous vein.

FIGS. 18A-B show that preincubation with papaverine inhibits histamine and KCl induced contractions in porcine coronary artery.

FIGS. 19A-B show that preincubation with papaverine inhibits norepinephrine induced contractions in human saphenous vein.

DETAILED DESCRIPTION OF THE INVENTION

Figure 1:
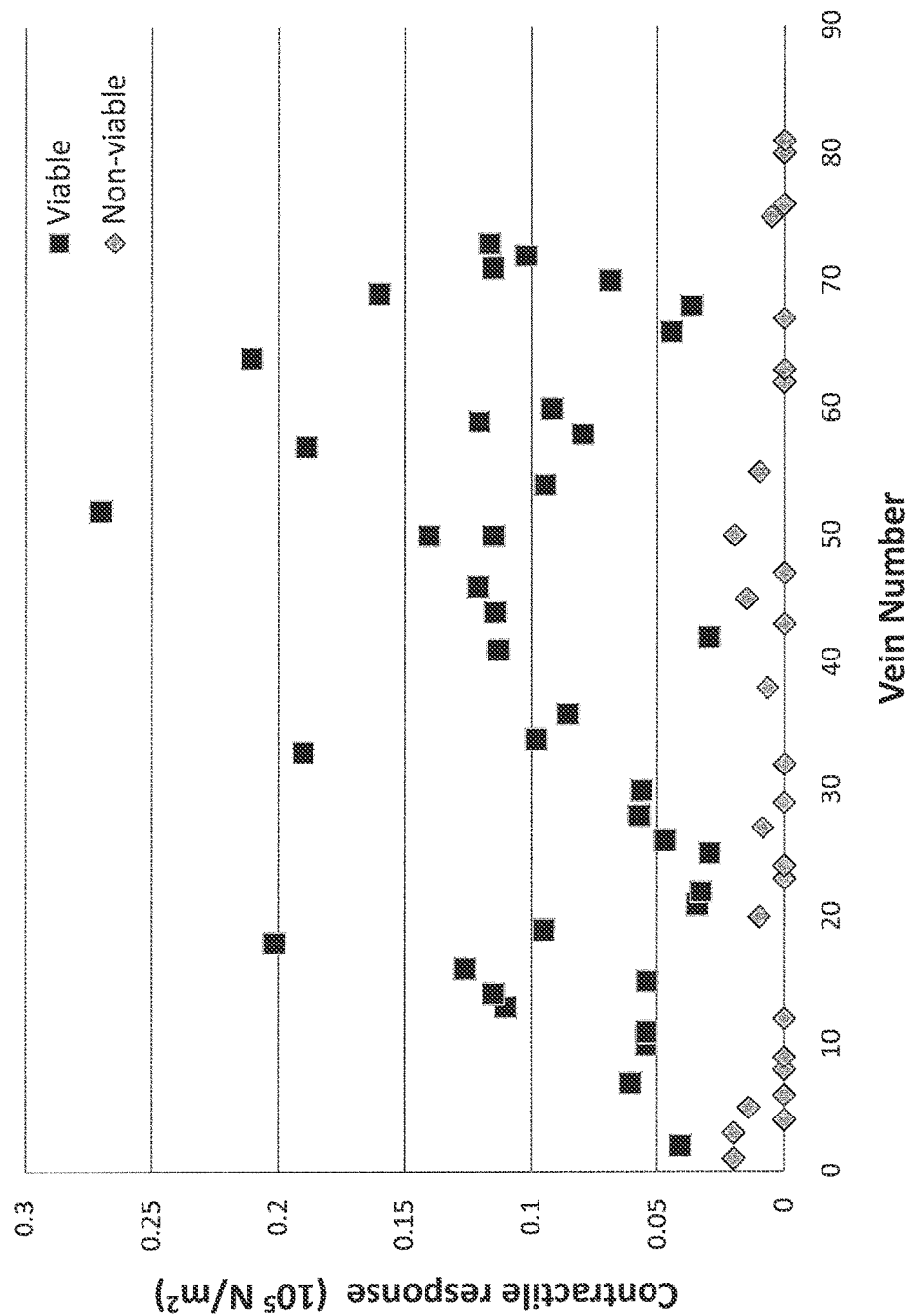
FIG. 1 shows the variable smooth muscle functional viability in human saphenous vein.

Thus, the present invention provides new methods and reagents with which to harvest, treat, preserve and transplant autologous conduits and inhibit intimal hyperplasia. The pH of the solution used to store autologous vein conduits prior to implantation, which includes heparinized saline, is highly acidic (pH 6.2). This acidic pH has been shown to reduce the functionality of the conduit. Moreover, the use of surgical skin markers comprising isopropyl alcohol, to mark the autologous conduits, also reduces the functionality of the conduit. Erioglaucine, otherwise known as FD&C blue dye #1, is not toxic to the vein and restores functional integrity after injury. It also has been shown that common manual distension of the vein can lead to intraluminal pressures greater than 300 mm Hg, which also has a deleterious effect on conduit functionality. Placing a pop off valve on the syringe reduces the maximal possible intraluminal pressure to 130-140 mm Hg, thereby protecting the vein conduit.

I. HARVEST SOLUTION

In one aspect, the present invention provides a buffered solution, pH 7.0-7.6, in which to place the vein after harvest. In one embodiment the buffer is phosphate buffered saline; however, MOPS, Hepes, Pipes, and acetate are alternative formulations. Magnesium sulfate (5 mM) can also be added to the solution to stabilize membranes.

Another buffer option is Plasma-Lyte 56 Injection (Multiple Electrolytes Injection, Type 1, USP) a sterile, nonpyrogenic, hypotonic solution in a single dose container for intravenous administration. Each 100 mL contains 234 mg of Sodium Chloride, USP (NaCl); 128 mg of Potassium Acetate, USP ($C_2H_3KO_2$); and 32 mg of Magnesium Acetate Tetrahydrate ($Mg(C_2H_3O_2)2.4H_2O$). It contains no antimicrobial agents. The pH is adjusted with hydrochloric acid.

In another aspect of the invention, the harvest solution can be prepared as a highly viscous solution such as that described in Seal & Panitch (2003). These authors described a rapidly forming polymer matrix with affinity-based controlled release properties was developed based upon interactions between heparin-binding peptides and heparin. Dynamic mechanical testing of 10% (w/v) compositions consisting of a 3:1 molar ratio of poly(ethylene glycol)-co-peptide (approximately 18,000 g/mol) to heparin (approximately 18,000 g/mol) revealed a viscoelastic profile similar to that of concentrated, large molecular weight polymer solutions and melts. In addition, the biopolymer mixtures recovered quickly following thermal denaturation and mechanical insult. These gel-like materials were able to sequester exogenous heparin-binding peptides and could release these peptides over several days at rates dependent on relative heparin affinity. The initial release rates ranged from 3.3% per hour for a peptide with low heparin affinity to 0.025% per hour for a peptide with strong heparin affinity. By altering the affinity of peptides to heparin, a series of peptides can be developed to yield a range of release profiles useful for controlled in vivo delivery of therapeutics.

II. SUPPLEMENTAL SOLUTION ADDITIVES

In another aspect of the invention, the solutions of the present invention may contain additional additives to address various protective aspects of the invention.

For example, the solutions of the present invention may include heparin (1-10 U/ml) to prevent thrombus formation. Heparin is a highly sulfated glycosaminoglycan that is widely used as an injectable anticoagulant, and has the highest negative charge density of any known biological molecule. It can also be used to form an inner anticoagulant surface on various experimental and medical devices such as test tubes and renal dialysis machines. Pharmaceutical grade heparin is derived from mucosal tissues of slaughtered meat animals such as porcine (pig) intestine or bovine (cow) lung.

Although used principally in medicine for anticoagulation, the true physiological role of heparin in the body remains unclear, because blood anti-coagulation is achieved mostly by endothelial cell-derived heparan sulfate proteoglycans. Heparin is usually stored within the secretory granules of mast cells and released only into the vasculature at sites of tissue injury. It has been proposed that, rather than anticoagulation, the main purpose of heparin is in a defensive mechanism at sites of tissue injury against invading bacteria and other foreign materials. In addition, it is preserved across a number of widely different species, including some invertebrates that do not have a similar blood coagulation system.

Native heparin is a polymer with a molecular weight ranging from 3 kDa to 50 kDa, although the average molecular weight of most commercial heparin preparations is in the range of 12 kDa to 15 kDa. Heparin is a member of the glycosaminoglycan family of carbohydrates (defined as an organic compound which has the empirical formula Cm(H2O)n; that is, consists only of carbon, hydrogen and oxygen, with a hydrogen:oxygen atom ratio of 2:1). Glycosaminoglycans (GAGs) or mucopolysaccharides are long unbranched polysaccharides consisting of a repeating disaccharide unit. The repeating unit consists of a hexose (six-carbon sugar) or a hexuronic acid, linked to a hexosamine (six-carbon sugar containing nitrogen).

Heparin, (which includes the closely-related molecule heparan sulfate) consists of a variably-sulfated repeating disaccharide unit. The main disaccharide units that occur in heparin are shown below. The most common disaccharide unit is composed of a 2-O— sulfated iduronic acid and 6-O-sulfated, N-sulfated glucosamine, IdoA(2S)-GlcNS (6S). For example, this makes up 85% of heparins from beef lung and about 75% of those from porcine intestinal mucosa. Not shown below are the rare disaccharides containing a 3-O-sulfated glucosamine (GlcNS(3S,6S)) or a free amine group (GlcNH$_3^+$). Under physiological conditions, the ester and amide sulfate groups are deprotonated and attract positively-charged counterions to form a heparin salt. It is in this form that heparin is usually administered as an anticoagulant.

In another aspect, the harvest solution can be a hydrogel that coats the vessel to minimize volume while keeping the vessel moist. In addition, the hydrogel can contain a therapeutic to help maintain vasorelaxation. Hydrogels include those synthesized from hydrophilic polymers that are cross-linked through covalent bods such as poly (ethylene glycol), polyacrylamide, polyfumerate, poly(N-siopropyl acrylamide), etc., or any gel like material crosslinking through physical interactions including hydrophobic and ionic. Gels include polyurethanes, agarose and alginates.

In another aspect of the invention, the present invention includes papaverine (1 mM) to inhibit contraction and spasm of the vein. Alternative anti-spasmodic agents are nicardipine, sodium nitroprusside, nitroglycerine (0.5-1.0 mM), or dibutyryl cAMP (2 mM).

In another aspect of the invention, the present invention includes antioxidants to prevent oxidative damage to the vein. N-acetylcysteine (10 mM), allopurinol (1 mM), glutathione (3 mM), mannitol (30-60 mM), or green tea phenols (0.5-1.0 mg/ml) are particular antioxidants of interest.

In another aspect, the present invention provides oligosaccharides in the harvest solution to prevent desiccation of the graft. Lactobionic acid (100 mM), raffinose (30 mM), or trehalose (30 mM) are particular oligosaccharides. Lactobionic acid is a disaccharide that provides osmotic support and prevents cell swelling. Raffinose is a trisaccharide that provides hypertonicity. Trehalose is a disaccharide with water retention properties.

In another aspect, the present invention provides starch in the harvest solution to support colloid osmotic pressure. Hydroxyethyl starch (30-50 mM), dextran (40 g/l), blood, or albumin, are particularly contemplated colloid agents.

In another aspect of the invention, the present invention includes anti-inflammatory agents. Steroids such as dexamethasone (5-10 mg/l) or salicylic acid are examples of anti-inflammatory agents.

In another aspect of the invention, drugs will be included to prevent endothelial dysfunction. Angiotensin converting enzyme inhibitors, statins, metformin, AICAR and estrogens are examples of such drugs.

In another aspect of the invention, the present invention includes metabolic regulators. Glucose (200 mM), adenosine (5 mM), and insulin (100 U/ml) are particularly contemplated metabolic regulators.

In another aspect of the invention, the present invention includes a novel peptide inhibitor of MAPKAP kinase 2 (and related peptides) to reduce inflammation, enhance relaxation of the smooth muscle, and prevent spasm. PCT Applications US2007/16246 and US2008/72525 describe such inhibitors, and are incorporated by reference herein.

In another aspect of the invention, the present invention includes siRNA or miRNA to decrease the expression of HSP27 to prevent intimal hyperplasia. The sense strand siRNA sequences are 1) GACCAAGGAUGGCGUGGU-GUU (SEQ ID NO: 1) and 2) AUACACGCUGCCCCCCG-GUUU (SEQ ID NO: 2). The sense strand miRNA sequences are 1) miR-580 or miR-1300, AACUCUUAC-UACUUAGUAAUCC (SEQ ID NO: 3) and 2) miR-552, UUGUCCACUGACCAAUCUGUU (SEQ ID NO: 4). The anti-miR-320 sequence is: UCGCCCUCUCAACCCAGC-UUUU (SEQ ID NO: 5). Expression of the siRNA and miRNA is plasmid based or synthetic. Delivery of the DNA or synthetic oligo-duplexes can be performed via reversible permeabilization or pressurization (Monahan et al., 2009).

III. P2X$_7$ RECEPTOR ANTAGONISTS

Injury leads to prolonged release of ATP which can activate ATP receptors (Khakh & North, 2006). P2X receptors are a family of ligand-gated ion channels that bind extracellular ATP. The $P2X_7$ receptor is responsible for the ATP-dependent lysis of macrophages and is also found on human saphenous vein smooth muscle (Cario-Toumaniantz et al., 1998). Activation of the $P2X_7$ receptor can form membrane pores permeable to large molecules in human saphenous vein (Cario-Toumaniantz et al., 1998). This leads to increases in intracellular $Ca^{2+}$ which can activate caspases, and ultimately lead to cell death due to autolysis and apoptosis (Donnelly-Roberts et al., 2004). Activation of the $P2X_7$ receptor has been associated with activation of p38 MAPK pathway and changes in the actin cytoskeleton (Pfeiffer et al., 2004). Activation of $P2X_7$ receptor also leads to production and release of interleukins and other cytokines which contributes to an inflammatory response (Donnelly-Roberts et al., 2004). Recently, systemic administration of an antagonist of the $P2X_7$ receptor has been shown to improve recovery in a rodent model of stretch induced spinal cord injury (Peng et al., 2009).

A variety of $P2X_7$ receptor antagonists have been described in the literature. For example, Alcaraz et al. (2003) describe the synthesis and pharmacological evaluation of a series of potent $P2X_7$ receptor antagonists. The compounds inhibit BzATP-mediated pore formation in THP-1 cells. The distribution of the $P2X_7$ receptor in inflammatory cells, most notably the macrophage, mast cell and lymphocyte, suggests that $P2X_7$ antagonists have a significant role to play in the treatment of inflammatory disease. Carroll et al. (2009) review distinct chemical series of potent and highly selective $P2X_7$ receptor antagonists.

The following U.S. patents, incorporated herein by reference, disclose $P2X_7$ receptor antagonists: U.S. Pat. Nos. 7,709,469, 6,812,226, 7,741,493 7,718,693 and 7,326,792. The following U.S. Patent Publications, incorporated herein by reference, disclose $P2X_7$ receptor antagonists: 2010/0292295, 2010/0292224, 2010/0286390, 2010/0210705, 2010/0168171, 2010/0160389, 2010/0160388, 2010/0160387, 2010/0160384, 2010/0160373, 2010/0144829, 2010/0144727, 2010/0105068, 2010/0075968, 2010/0056595, 2010/0036101, 2009/0264501, 2009/0215727, 2009/0197928, 2009/0149524, 2009/0005330, 2008/0132550, 2008/0009541, 2007/0122849, 2007/0082930, 2005/0054013, 2005/0026916 and 2002/0182646.

As discussed above, an aspect of the invention includes a marker that contains a non-toxic dye to mark the vein. FD&C Blue #1 (erioglaucine), an artificial food dye approved by the FDA (E #133), also has not only been shown to be non-toxic, but protective of harvest techniques that are injurious to saphenous veins and is a $P2X_7$ receptor antagonist. Brilliant blue G, an analog erioglaucine, also is contemplated as a $P2X_7$ receptor antagonist.

Indigotine (E132) is another dark blue artificial dye approved by the FDA. Fast Green (E143) is another bluish green artificial dye approved by the FDA. Natural dyes such as curcumrin or betanin are other alternatives. Curcumin is the principal curcuminoid of the spice tumeric and has antioxidant and anti-inflammatory properties. As a food additive, its E number is E100. Betanin is a red glycosidic food dye obtained from beets and is a natural food dye. Other possible dyes include genestein blue, evans blue, india ink, Allura Red AC, Tartazine, and Erythrosine.

IV. DEVICES

Preliminary studies, discussed below, demonstrate that currently used harvest techniques are injurious to saphenous veins. These data pose a new paradigm for thinking about vein graft failure and offer simple and straightforward approaches to ameliorate vein graft injury.

Thus, in another aspect of the invention, the present invention includes a "pop off" valve to prevent over distension of the vein during side branch ligation. Qosina pressure relief T valve (part #D002501) is one example. In another aspect of the invention, the present invention includes a "bullet tipped" needle that is used to secure the vein and a device to prevent stretch of the vein.

V. KITS

The present invention may also be embodied in a kit for use in conjunction with surgical vein transplant procedures. The immunodetection kits will comprise, in suitable container means, various containers, devices and/or reagents, along with appropriate instructions for use.

In certain embodiments, the kit will comprise harvest solutions, or reagents for making such. The solutions or reagents would be provided in sterile form, optionally with sterile containers for mixing and storing harvest solutions. The kit may also advantageously comprise a chamber for bathing/storing transplant tissue following explant and prior to transplant. Various other supplemental additives described above may also be included.

Another element of the kit may be the inclusion of a surgical marking pen comprising a non-toxin dye/marker, as described above. The pen may be "preloaded" with the marker/dye, or may be provided empty, with the marker/dye in solution or in reagent form to be loaded into the pen by the user.

Further devices including a syringe, catheter, and/or tubing equipped or including a pop-off valve as described above. Also included may be a device for holding a vein in place, such as a clamp, optionally provided with a stand or base, permitting "hands-free" positioning of the graft for further treatment.

The container aspect of the kit will generally include means for holding at least one vial, test tube, flask, bottle, packet, syringe, catheter or other container in a secure and protected fashion, for example, in close confinement for commercial sale. Such means may include injection or blow-molded plastic containers into which the desired containers, devices or reagents are retained.

VI. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Toxicity of Surgical Marking Pens to Vein Tissue

De-identified discarded segments of human saphenous vein were collected (n=66), after informed consent approved by the Institutional Review Board of the Vanderbilt University (Nashville, Tenn.), from patients undergoing coronary artery bypass or peripheral vascular bypass surgery. The veins were stored in a saline solution until the end of the surgical procedure at which time they were placed in cold transplant harvest buffer (100 mM potassium lactobionate, 25 mM $KH_2PO_4$, 5 mM $MgSO_4$, 30 mM raffinose, 5 mM adenosine, 3 mM glutathione, 1 mM allopurinol, 50 g/L hydroxyethyl starch, pH 7.4) and stored at 4° C. The vessels were tested within 24 hours of harvest. The presense of blue markings were assessed for each HSV. Rings 1.0 mm in width were cut from segments of saphenous vein dissected free of fat and connective tissue, stripped of the endothelium and were suspended in a muscle bath containing a bicarbonate buffer (120 mM NaCl, 4.7 mM KCl, 1.0 mM $MgSO_4$, 1.0 mM $NaH_2PO_4$, 10 mM glucose, 1.5 mM $CaCl_2$, and 25 mM $Na_2HCO_3$, pH 7.4), gassed with 95% $O_2$/5% $CO_2$ at 37° C. The rings were manually stretched to 4 g of tension, and was maintained at a resting tension of 1 g was obtained and equilibtrated for ~2 hr. Force measurements were obtained using a Radnoti Glass Technology (Monrovia, Calif.) force transducer (159901A) interfaced with a Powerlab data acquisition system and Chart software (AD Instruments, Colorado Springs, Colo.). To determine viability, the rings were contracted with 110 mM KCl (with equimolar replacement of NaCl in bicarbonate buffer), and the force generated was measured. Force was converted to stress ([Newtons $(N)/m^2$]=force (g)×0.0987/area, where area is equal to the wet weight [mg/length (mm at maximal length)] divided by 1.055) $10^5$ $N/m^2$. There was variability in the functional viability of the veins (FIG. 1). Veins generating stress of $\leq 0.025 \times 10^5$ $N/m^2$ were considered non-viable (grey) and those generating stress of $>0.025 \times 10^5$ $N/m^2$ were viable (black). 40% of the vein tested was non-viable. Each point represents a different patient and an aggregate of at least three separate rings from that patient.

Figure 2:
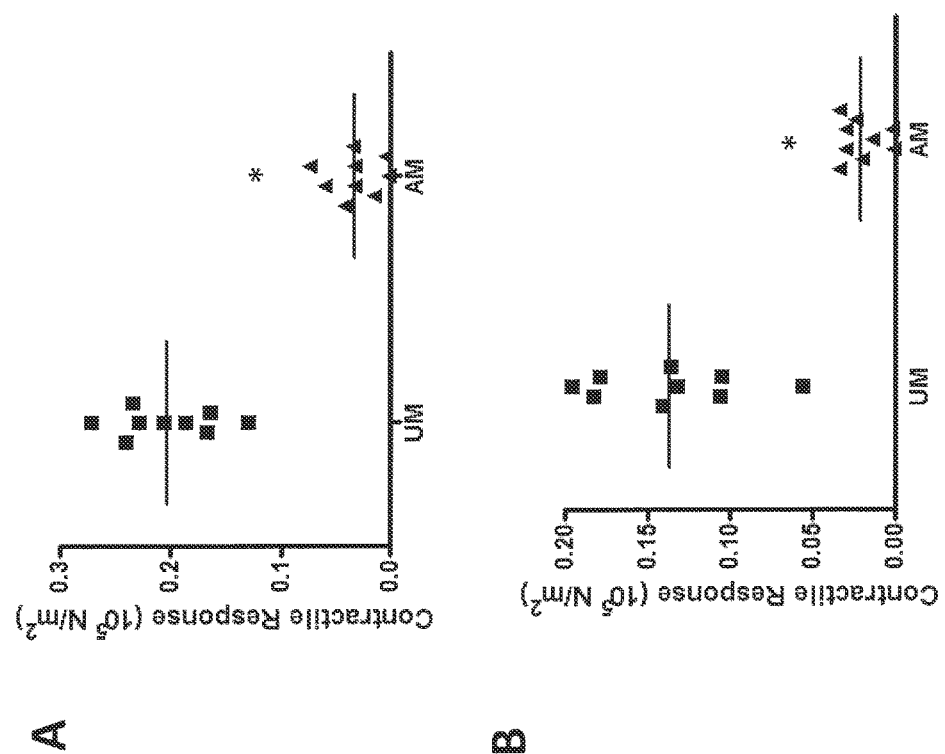
FIGS. 2A-B show that the current surgical harvest techniques lead to decreased smooth muscle functional viability.

Segments of human saphenous vein (n=8) were collected prior to preparation of the vein for transplantation into the arterial circulation (unmanipulated, UM) and after surgical preparation (after manipulation, AM). Preparation involves manual distension of the vein, marking with a surgical skin marker, and placing the vein in heparinized saline. The contractile response to 110 mM KCl (FIG. 2A) or phenylephrine ($10^{-6}$M, FIG. 2B) was determined and force generated was converted to stress ($10^5$ $N/m^2$). Manipulation during vein preparation led to decreased contractile response to KCl and phenylephrine (FIGS. 2A-B). Each point represents a different patient and an aggregate of the response of at least three separate rings from each patient.

Figure 3:
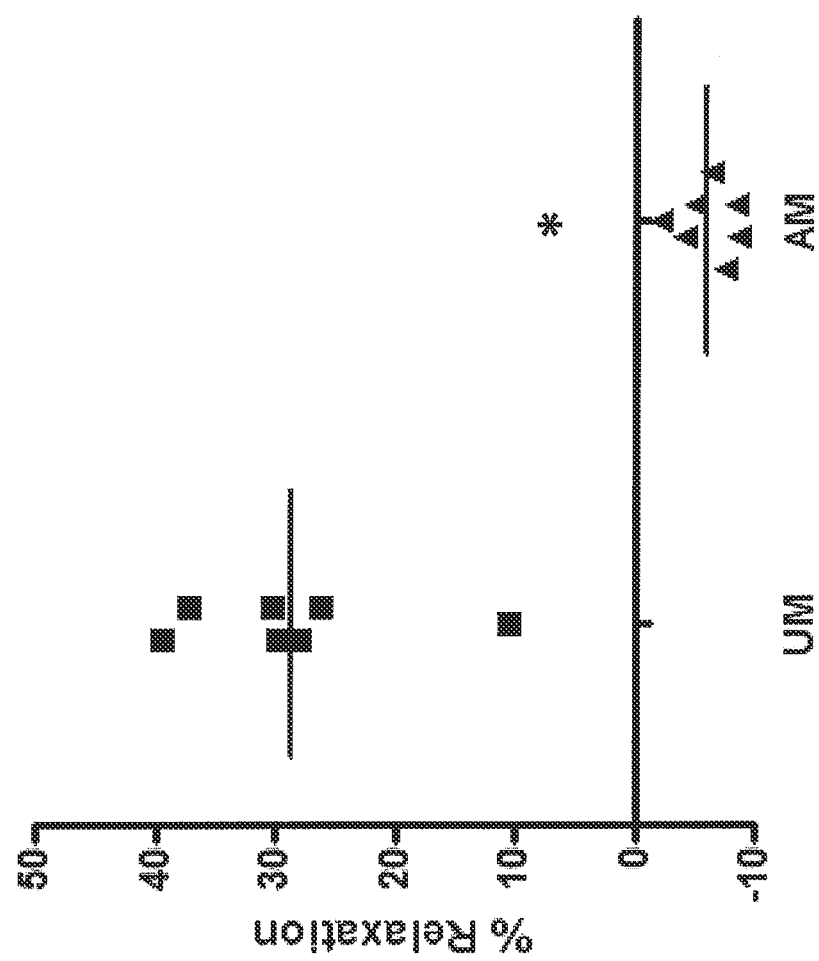
FIG. 3 demonstrates that the current surgical harvest techniques lead to reduced endothelial functional viability.

Human saphenous veins were also precontracted with phenylephrine ($10^{-6}$M) followed by treatment with carbachol ($5 \times 10^{-7}$M) to determine endothelial dependent relaxation (Furchgott et al., 1980). Segments of human saphenous vein (n=5) were collected prior to preparation of the vein for transplantation into the arterial circulation (unmanipulated, UM) and after surgical preparation (after manipulation, AM). Rings from each segment were suspended in a muscle bath, equilibrated in a bicarbonate buffer, and contracted with 110 mM KCl. After an additional 30 min equilibration in a bicarbonate buffer, rings were pre-contracted with $10^{-6}$M phenylephrine (PE) and treated with $5 \times 10^{-7}$M carbachol. Force was measured and converted to stress $10^5$ $N/m^2$. Responses were expressed as % of maximum PE-induced contraction. Typical manipulation during surgical preparation led to reduced endothelial-dependent relaxation (FIG. 3). UM veins had 28.74±3.542% endothelial-dependent relaxation whereas AM contracted in response to carbachol (−5.976±0.9172%).

Human saphenous veins were also precontracted with phenylephrine ($10^{-6}$ M) followed by treatment with sodium nitroprusside ($10^{-7}$M) to determine endothelial independent relaxation. Segments of saphenous vein (n=6) were collected prior to harvest preparation (unmanipulated, UM) or after harvest preparation (after manipulation, AM). Rings from each segment were suspended in a muscle bath, equilibrated in a bicarbonate buffer, and contracted with 110 mM KCl. After an additional 30 min equilibration in a bicarbonate buffer, rings were pre-contracted with $10^{-6}$M phenylephrine (PE) and treated with $10^{-7}$M sodium nitroprusside. Typical manipulation during surgical preparation reduced endothelial-independent relaxation of human saphenous vein (FIGS. 4A-B). Representative force tracings of the UM and AM segments collected from the same patient in response to PE and SNP (FIG. 4A). The endothelial independent relaxation displayed by the two groups, expressed as % of maximum PE-induced contraction, were significantly different. UM veins displayed an 86.62+/−5.986% relaxation, whereas AM veins displayed a 4.292+/−1.397% relaxation (FIG. 4B).

Figure 5:
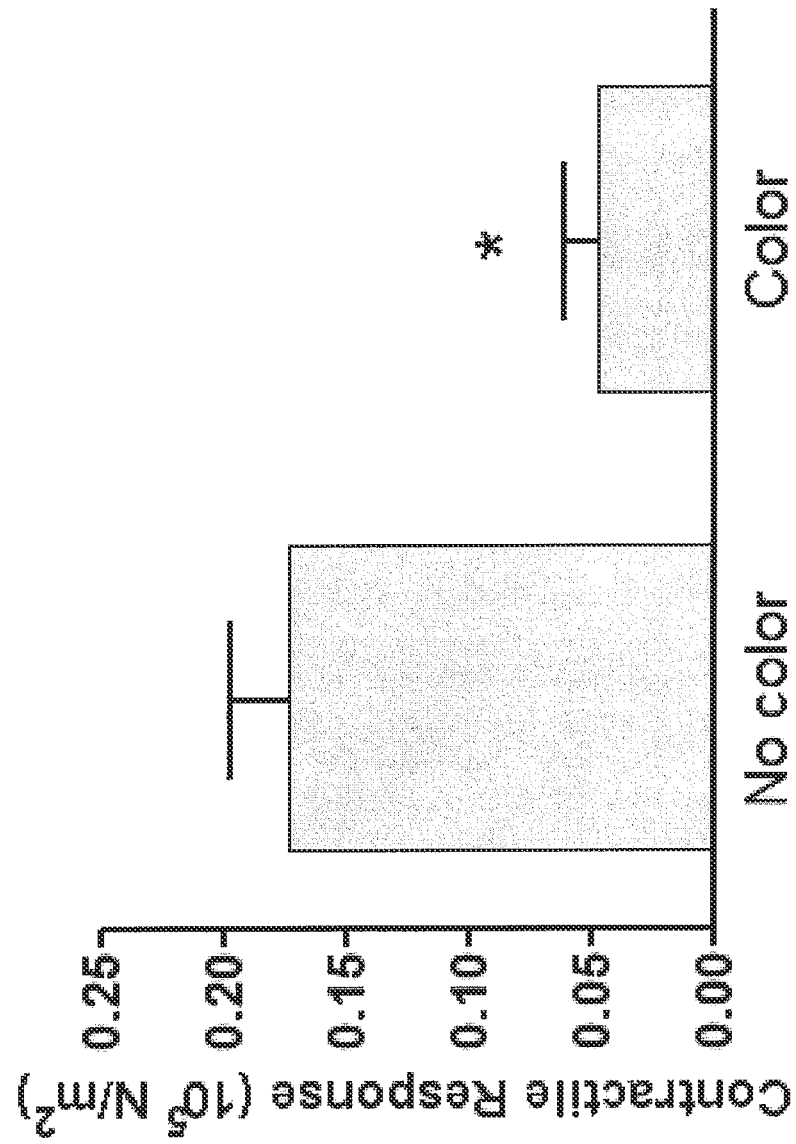
FIG. 5 demonstrates that human saphenous vein grafts with blue markings displayed reduced smooth muscle functional viability.

Of the 38 veins collected from patients undergoing coronary artery bypass or peripheral vascular revascularization surgery, 16 of the veins did not have any visible color by surgical marking pen whereas 22 of the veins had visible color. Rings were cut from the veins, suspended in a muscle bath and equilibrated in bicarbonate buffer. The rings were contracted with 110 mM KCl and force generated was converted to stress ($10^5$ $N/m^2$). The force generated by the two groups of veins were significantly different (FIG. 5). Veins that had visible blue marking displayed less contractile responses (0.047±0.014 $10^5$ $N/m^2$) than veins that had no visible marking (0.174±0.023 $10^5$ $N/m^2$).

Figure 6:
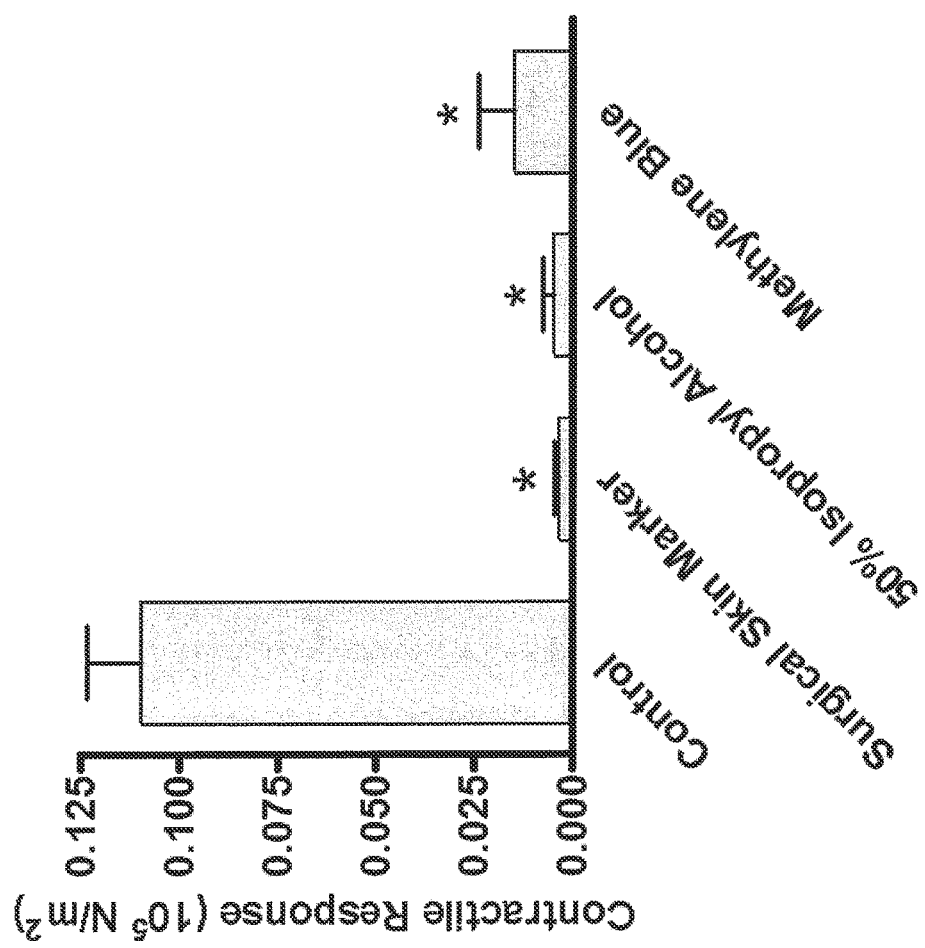
FIG. 6 demonstrates that surgical skin marking reduced smooth muscle viability of human saphenous vein.

De-identified discarded segments of human saphenous vein that did not have any color were used to test the effect of different marking methods. Rings cut from the segments were either left unmarked (control; n=12), marked with a surgical skin marker (Cardinal Health, #5227 violet marking ink; n=5), marked in 50% isopropyl alcohol, a solvent used in the skin marker (n=4), or marked with methylene blue (Akorn, Inc., Lake Forest Ill. n=10) and incubated for 15 min at room temperature. The rings were stripped of the endothelium and were suspended in a muscle bath containing a bicarbonate buffer (120 mM NaCl, 4.7 mM KCl, 1.0 mM $MgSO_4$, 1.0 mM $NaH_2PO_4$, 10 mM glucose, 1.5 mM $CaCl_2$, and 25 mM $Na_2HCO_3$, pH 7.4), gassed with 95% $O_2$/5% $CO_2$ at 37° C. The rings were manually stretched to 4 g of tension, and were maintained at a resting tension of 1 g and equilibtrated for ~2 hr. Force measurements were obtained using a Radnoti Glass Technology (Monrovia, Calif.) force transducer (159901A) interfaced with a Powerlab data acquisition system and Chart software (AD Instruments, Colorado Springs, Colo.). The rings were contracted with 110 mM KCl (with equimolar replacement of NaCl in bicarbonate buffer), and the force generated was converted to stress $10^5$ $N/m^2$. The three marked groups were significantly different from the control unmarked group ($p \leq 0.05$) (FIG. 6). The rings that did not have markings had an average stress of 0.110±0.014 $10^5$ $N/m^2$, the rings that were marked with the surgical skin marker had an average stress of 0.003±0.00110$^5$ $N/m^2$, rings marked with 50% isopropyl alcohol had an average stress of 0.005±0.003 $10^5$ $N/m^2$, and rings marked with methylene blue had an average stress of 0.014±0.01 $10^5$ $N/m^2$.

Figure 7:
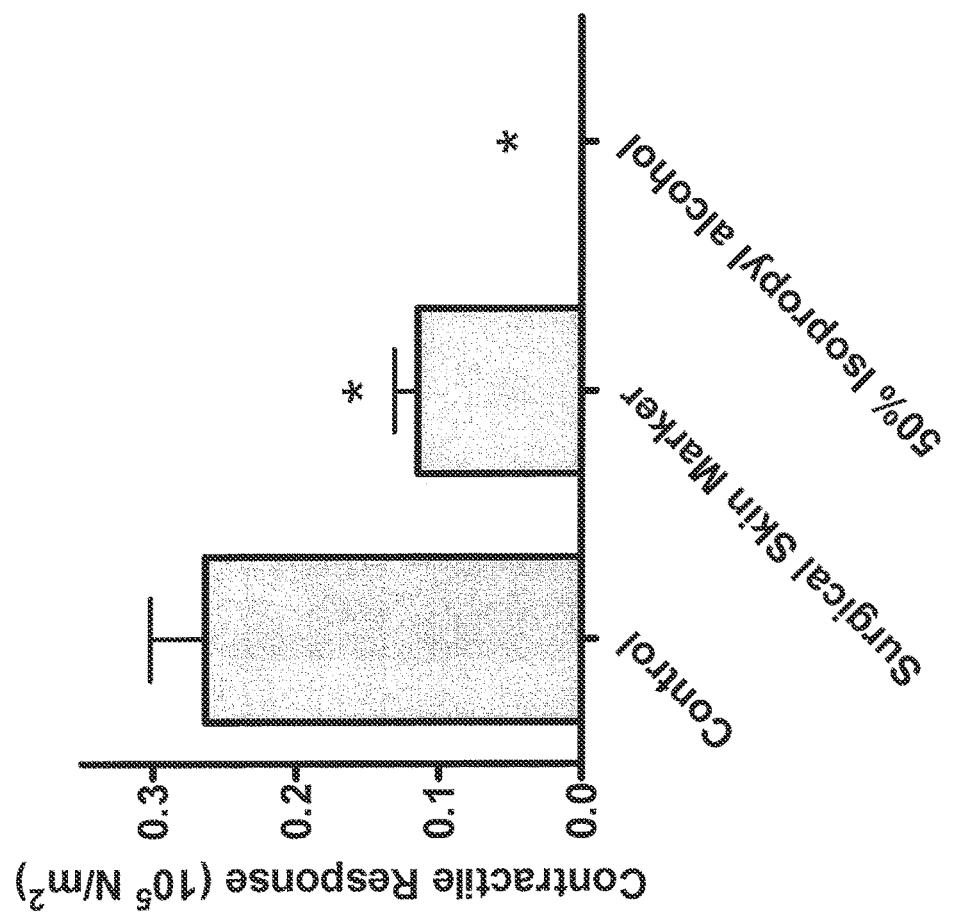
FIG. 7 shows surgical skin marking pens reduce the viability of pig saphenous vein.

Freshly isolated porcine saphenous veins were used to test the effect of different marking methods. The veins were collected and placed in cold transplant harvest buffer [100 mM potassium lactobionate, 25 mM $KH_2PO_4$, 5 mM $MgSO_4$, 30 mM raffinose, 5 mM adenosine, 3 mM glutathione, 1 mM allopurinol, 50 g/L hydroxyethyl starch, pH 7.4]. The vessels were stored in transplant harvest buffer at 4° C. and tested within 24 hours of harvest and. To test the viability, rings 1.0 mm in width were cut from segments of saphenous vein and dissected free of fat and connective tissue. Saphenous vein rings were untreated (Control; n=6), marked with the surgical skin marker (n=3), or 50% isopropyl alcohol (the solvent used in the surgical marker; n=3) and incubated for 15 min at room temperature. The rings were then equilibrated in a muscle bath, contracted with KCl, and force was measured and converted to stress ($10^5$ $N/m^2$). The rings that did not have markings had an average stress of $0.263 \pm 0.039$ $N/m^2$, the rings that were marked with the surgical skin marker had an average stress of $0.114 \pm 0.017$ $N/m^2$, and rings marked with 50% isopropyl alcohol had an average stress of $0.00005 \pm 0.00005$ $N/m^2$. The two marked groups were significantly different from the control unmarked group ($p \leq 0.05$). (FIG. 7).

Example 2—Live Vein Cells Correlate with Functional Viability

A live cell assay was used to determined cellular viability of human saphenous vein. De-identified discarded segments of saphenous vein (n=13) were collected, after informed consent approved by the Institutional Review Board of the Vanderbilt University (Nashville, Tenn.), from patients undergoing coronary artery bypass or peripheral vascular bypass surgery. The veins were stored in a saline solution until the end of the surgical procedure at which time they were placed in cold transplant harvest buffer (100 mM potassium lactobionate, 25 mM $KH_2PO_4$, 5 mM $MgSO_4$, 30 mM raffinose, 5 mM adenosine, 3 mM glutathione, 1 mM allopurinol, 50 g/L hydroxyethyl starch, pH 7.4). The vessels were stored in transplant harvest buffer at 4° C. and tested within 24 hours of harvest. Each vein was subject to physiologic experiment and live cell assay using 3-(4,5-Dimethyl-2-thiazolyl)-2,5-diphenyl-2H-tetrazolium bromide (MTT). To test the viability, rings 1.0 mm in width were cut from segments of saphenous vein dissected free of fat and connective tissue, some were stripped of the endothelium and suspended in a muscle bath containing a bicarbonate buffer (120 mM NaCl, 4.7 mM KCl, 1.0 mM $MgSO_4$, 1.0 mM $NaH_2PO_4$, 10 mM glucose, 1.5 mM $CaCl_2$, and 25 mM $Na_2HCO_3$, pH 7.4), gassed with 95% $O_2$/5% $CO_2$ at 37° C. The rings were manually stretched to 4 g of tension, and was maintained at a resting tension of 1 g was obtained and equilibrated for ~2 hr. Force measurements were obtained using a Radnoti Glass Technology (Monrovia, Calif.) force transducer (159901A) interfaced with a Powerlab data acquisition system and Chart software (AD Instruments, Colorado Springs, Colo.). The rings were contracted with 110 mM KCl (with equimolar replacement of NaCl in bicarbonate buffer), and the force generated was measured. Any tissue failing to contract with KCl was considered non-viable. Force was converted to stress $10^5$ $N/m^2$ for each ring and was averaged for each vein. To assess cellular viability, three rings from each vein were placed separately in 0.25 ml of 0.1% MTT solution (prepared in Dulbecco phosphate buffered saline, pH 7.4). For negative control, one ring was placed in 20 ml of water and microwaved for 10 min to inactivate any enzymatic activity before placing in the 0.1% MTT solution. The rings were incubated at 37° C. for 1 hr. The reaction was stopped by placing the rings in distilled water. The tissues were weighed and placed in 1 ml of CelloSolve (Sigma) for 4 hours at 37° C. to extract the formazan pigment each. The concentration of the pigment was measured at 570 nm using a spectrophotometer (Beckman Coulter). The absorbance of the negative control was subtracted from each sample. The viability index was expressed as $OD_{570}$/mg/ml. The average for each vein was calculated from the three rings. The average stress obtained from each vein was then plotted against the average viability index.

Figure 8:
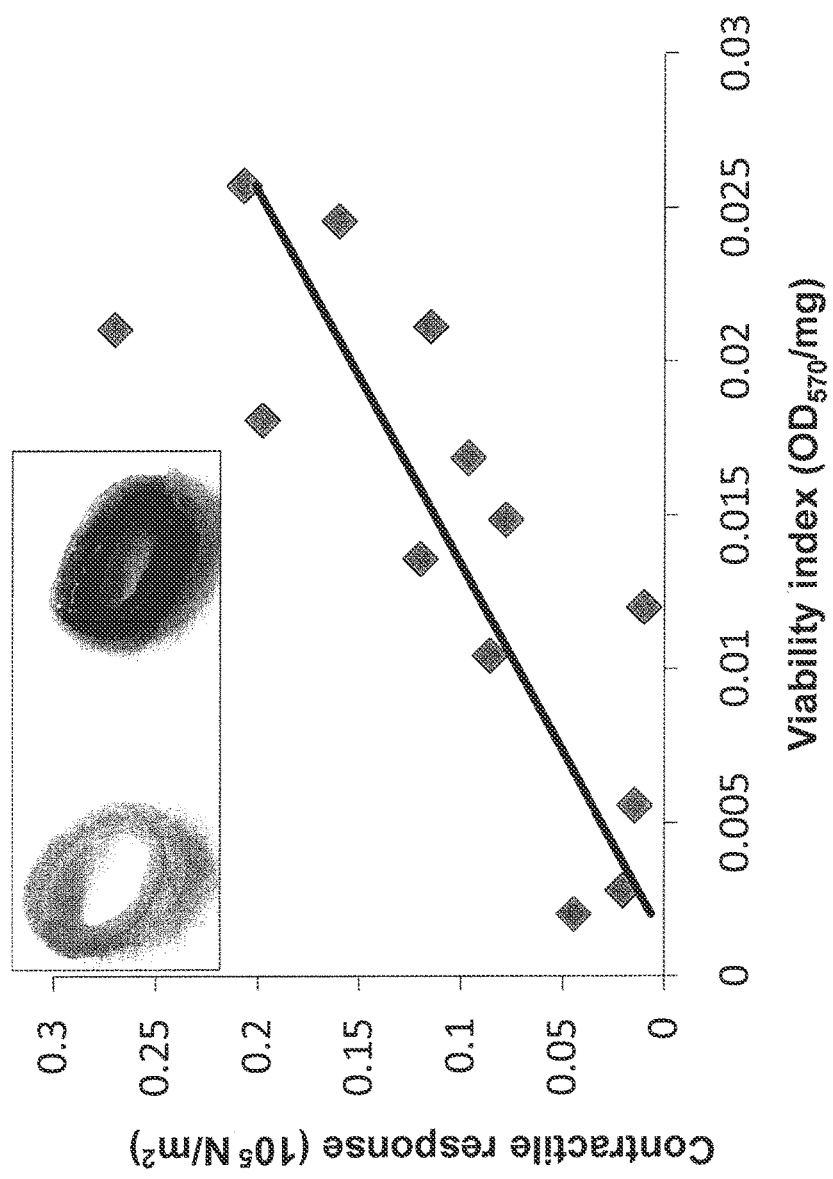
FIG. 8 shows functional response (contractile response to KCl) correlates with cell viability in human saphenous veins.

The data depict a significant slope showing that there was a proportional relationship ($R^2=0.7262$) between mitochondrial viability and the stress viability determined by the 110 mM KCl induced contraction (FIG. 8). Representative HSV rings of low (left) and high (right) viability index are shown in the inset.

Example 3—Vein Harvest Solutions and Procedures

Figure 9:
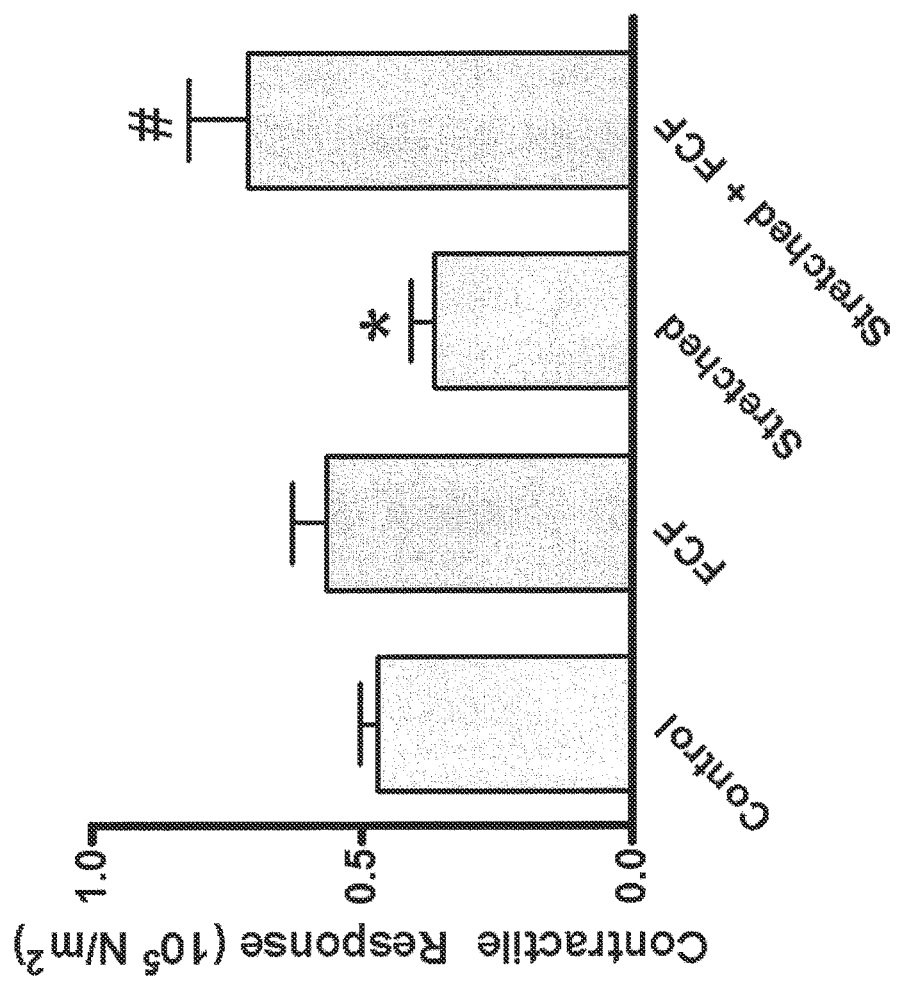
FIG. 9 demonstrates that erioglaucine restores functional viability after stretch injury in porcine saphenous vein.

Freshly isolated porcine saphenous vein was collected in cold transplant harvest buffer (100 mM potassium lactobionate, 25 mM $KH_2PO_4$, 5 mM $MgSO_4$, 30 mM raffinose, 5 mM adenosine, 3 mM glutathione, 1 mM allopurinol, 50 g/L hydroxyethyl starch, pH 7.4). The vessels were tested within 24 hours of harvest and storage in transplant harvest buffer at 4° C. The vein was dissected free of fat and connective tissue and cut into 2 cm long segments. The segments were stretched to twice their resting length (stretched; n=7) or not manipulated (control; n=12). After stretching, the segments from both groups were further divided. A solution of erioglaucine (FCF, 2.6 mM, in 5% propylene glycol and water) or vehicle was then applied with a cotton swab in a longitudinal line to the untreated (FCF; n=8) or the stretched (Stretched+FCF; n=3) vein segments. The segments were incubated at room temperature for 15 min in Plasmalyte and then cut into rings. The rings were suspended in a muscle bath containing a bicarbonate buffer (120 mM NaCl, 4.7 mM KCl, 1.0 mM $MgSO_4$, 1.0 mM $NaH_2PO_4$, 10 mM glucose, 1.5 mM $CaCl_2$, and 25 mM $Na_2HCO_3$, pH 7.4), bubbled with 95% $O_2$/5% $CO_2$ at 37° C. The rings were manually stretched to 4 g of tension, and maintained at a resting tension of 1 g and equilbrated for ~2 hr. Force measurements were obtained using a Radnoti Glass Technology (Monrovia, Calif.) force transducer (159901A) interfaced with a Powerlab data acquisition system and Chart software (AD Instruments, Colorado Springs, Colo. The rings were contracted with 110 mM KCl (with equimolar replacement of NaCl in bicarbonate buffer), and the force generated was converted to stress $10^5$ $N/m^2$ (FIG. 9). The control rings had an average stress of $0.47 \pm 0.034$ $N/m^2$, the rings that were marked with the erioglaucine dye had an average stress of $0.566 \pm 0.064$ $N/m^2$, and rings stretched had an average stress of $0.367 \pm 0.042$ $N/m^2$ and the stretched rings with erioglaucine dye had an average stress of $0.713 \pm 0.111$ $N/m^2$. The stress for the stretched vein was significantly (*$p<0.05$) different from the control unstretched veins and the stretched vein with erioglaucine dye was significantly (#$p<0.05$) different when compared to stretched without erioglaucine dye (FIG. 9).

Figure 10:
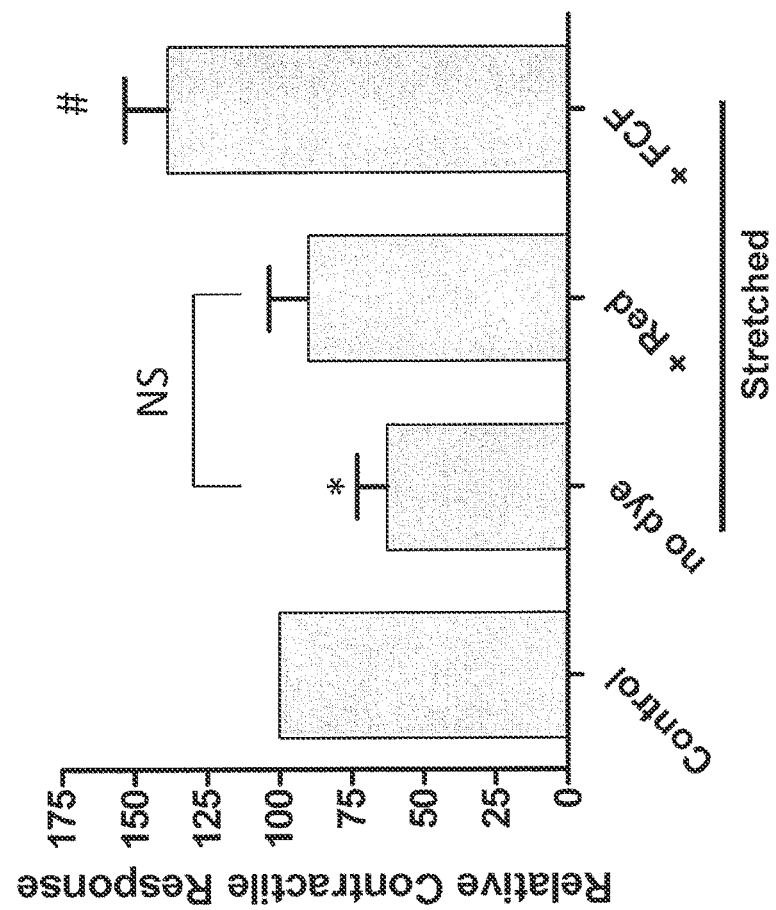
FIG. 10 shows that Allura Red did not restore stretch-induced injury in porcine saphenous veins.

However, treatment with another dye, Allura Red, did not restore functional viability after stretch injury of porcine saphenous vein (FIG. 10), Porcine saphenous veins (n=4) were left untreated (Control) or stretched to twice their resting length (no dye), cut into rings and suspended in the bicarbonate buffer in a muscle bath. Rings from stretched segments were either incubated with 50 μM Allura Red (+Red) or 50 μM of erioglaucine (+FCF) for 30 min. The rings were then allowed to equilibrate in the bicarbonate buffer for before contracting with 110 mM KCl. Force generated was converted to stress ($10^5$ $N/m^2$). Data represent relative contractile response to Control rings which was set as 100%. The stress for the stretched vein was not significantly different from the stretched vein with Allura Red (NS). Erioglaucine significantly restored contractile response in the stretched vein (#p≤0.05) when compared to the stretched vein with Allura Red.

Figure 11:
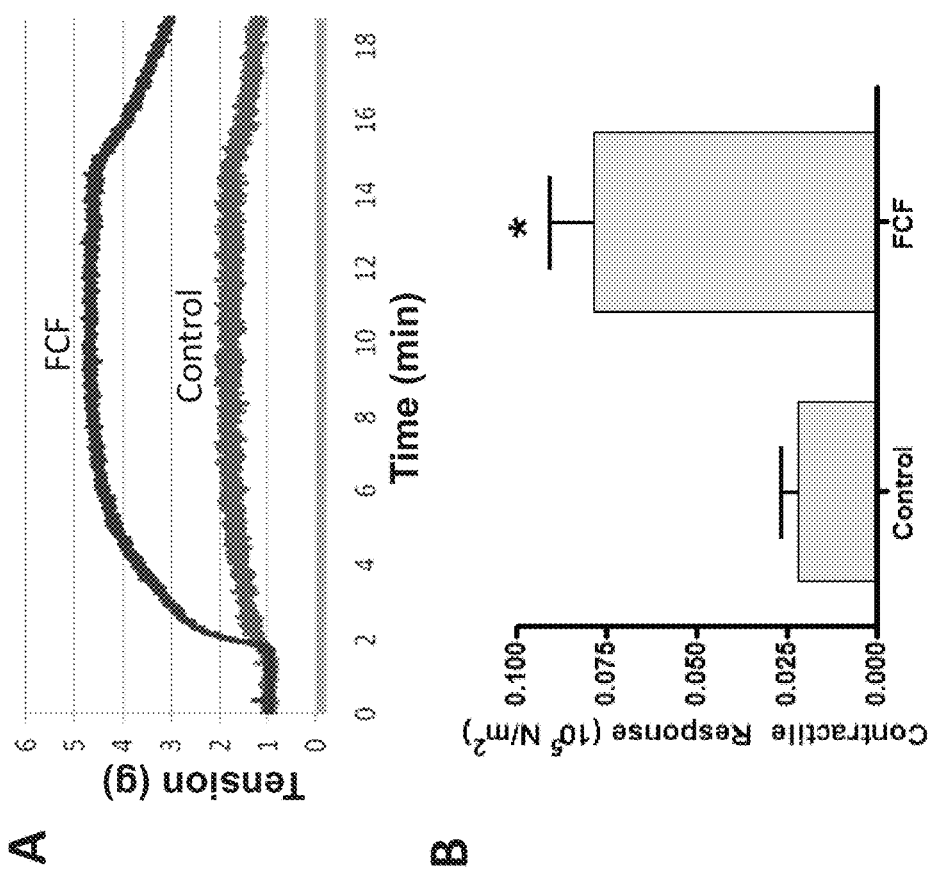
FIGS. 11A-B demonstrate that erioglaucine restores smooth muscle viability in human saphenous vein.

Effect of erioglaucine on human saphenous vein was determined using de-identified discarded segments of human saphenous vein from patients undergoing coronary artery bypass or peripheral vascular bypass surgery (n=4). The veins were stored in a saline solution until the end of the surgical procedure at which time they were placed in cold transplant harvest buffer (100 mM potassium lactobionate, 25 mM $KH_2PO_4$, 5 mM $MgSO_4$, 30 mM raffinose, 5 mM adenosine, 3 mM glutathione, 1 mM allopurinol, 50 g/L hydroxyethyl starch, pH 7.4). The vessels were tested within 24 hrs of harvest storage in transplant harvest buffer at 4° C. To test the viability, rings 1.0 mm in width were cut from segments of saphenous vein dissected free of fat and connective tissue, treated with either a solution of erioglaucine (FCF, 2.6 mM, in 5% propylene glycol and water) or vehicle and incubated for 30 min at room temperature. The tissues were then stripped of the endothelium and suspended in a muscle bath containing a bicarbonate buffer, gassed with 95% $O_2$/5% $CO_2$ at 37° C. The rings were manually stretched to 4 g of tension, and was maintained at a resting tension of 1 g was obtained and equilibrated for ~2 hr. Force measurements were obtained using a Radnoti Glass Technology (Monrovia, Calif.) force transducer (159901A) interfaced with a Powerlab data acquisition system and Chart software (AD Instruments, Colorado Springs, Colo.). The rings were contracted with 110 mM KCl (with equimolar replacement of NaCl in bicarbonate buffer), and the force generated was measured. Force was converted to stress $10^5$ $N/m^2$, and was plotted for vehicle and erioglaucine rings. Representative force tracings of rings left untreated (control) or treated with the erioglaucine dye (FCF) are depicted (FIG. 11A). The vehicle rings had an average stress of 0.015±0.012 $N/m^2$, and the erioglaucine-treated rings had an average stress of 0.103±0.021 $N/m^2$ (FIG. 11B). The two groups were significantly different (p≤0.05).

Figure 12:
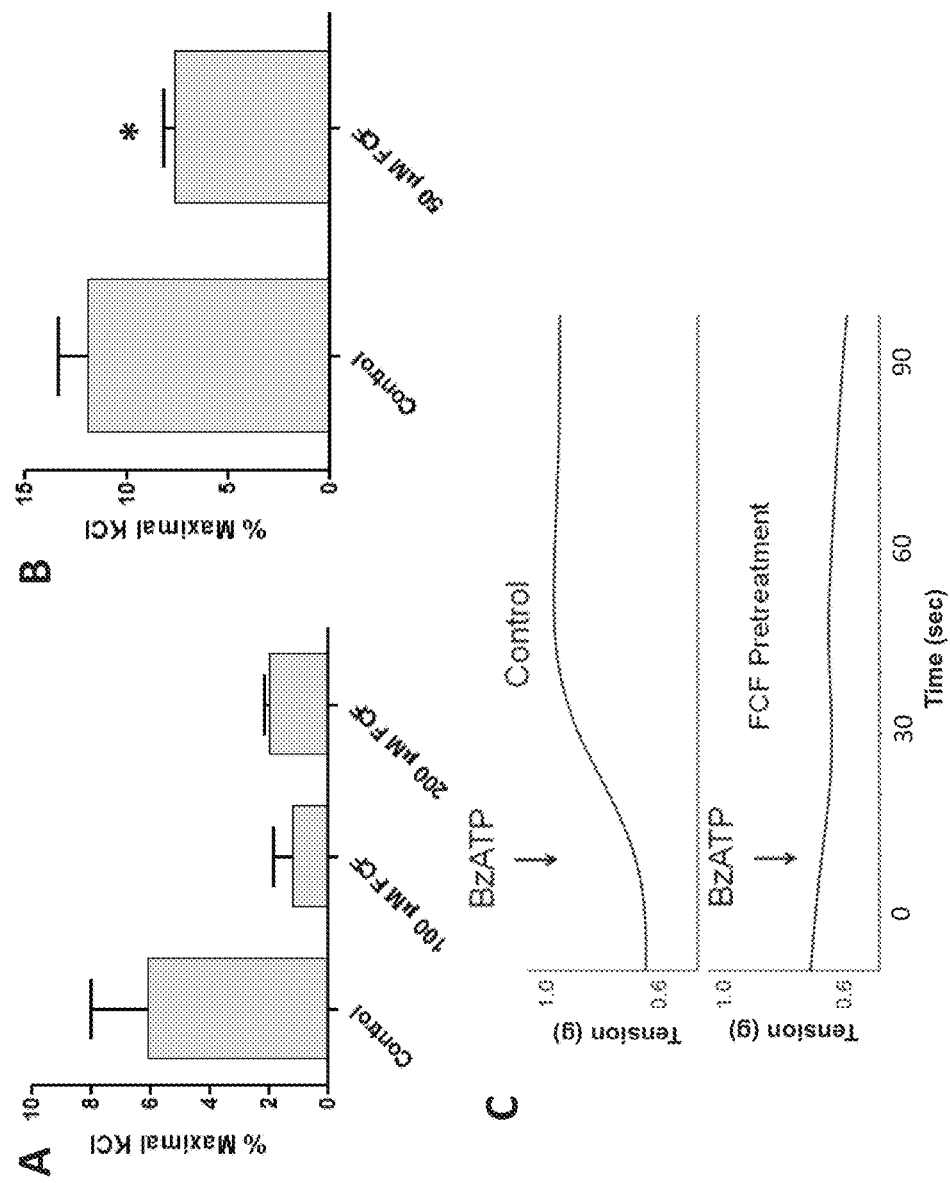
FIGS. 12A-C show that erioglaucine blocks BzATP-induced contraction in saphenous vein.

Human saphenous vein segments were collected after harvest before surgical manipulation from patients undergoing coronary artery bypass or peripheral vascular bypass surgery and stored in PlasmaLyte. The vessels were tested within 2 hours of harvest. Freshly isolated porcine saphenous vein was collected in cold transplant harvest buffer (100 mM potassium lactobionate, 25 mM $KH_2PO_4$, 5 mM $MgSO_4$, 30 mM Raffinose, 5 mM Adenosine, 3 mM Glutathione, 1 mM Allopurinol, 50 g/L Hydroxyethyl starch, pH 7.4). The vessels were tested within 24 hours of harvest. Rings 1.0 mm in width were cut from porcine saphenous veins (FIG. 12A, n=2) and unmanipulated human saphenous vein (FIG. 12B, n=4) dissected free of fat and connective tissue. The rings were then stripped of the endothelium and suspended in a muscle bath containing a bicarbonate buffer, bubbled with 95% $O_2$/5% $CO_2$ at 37° C. The rings were manually stretched to 4 g of tension, and was maintained at a resting tension of 1 g was obtained and equilibrated for ~2 hr. Force measurements were obtained using a Radnoti Glass Technology (Monrovia, Calif.) force transducer (159901A) interfaced with a Powerlab data acquisition system and Chart software (AD Instruments, Colorado Springs, Colo.). Rings were contracted with 110 mM KCl. After an additional 30 min equilibration, rings were treated with either a solution of erioglaucine (FCF, 50-200 µM for 30 minutes) or vehicle for 30 min and then contracted with 100 µM BzATP. Force was measured and converted to stress. Response was expressed as % of maximal KCl contraction. Representative force tracing of human saphenous vein contracted with BzATP after pretreatment with vehicle (control) or 50 µM erioglaucine (FCF pretreatment) are depicted in FIG. 12C. Pretreatment with erioglaucine (FCF) but not the vehicle (Control) significantly inhibited BzATP induced contraction (*p<0.05) (FIG. 12B).

Figure 13:
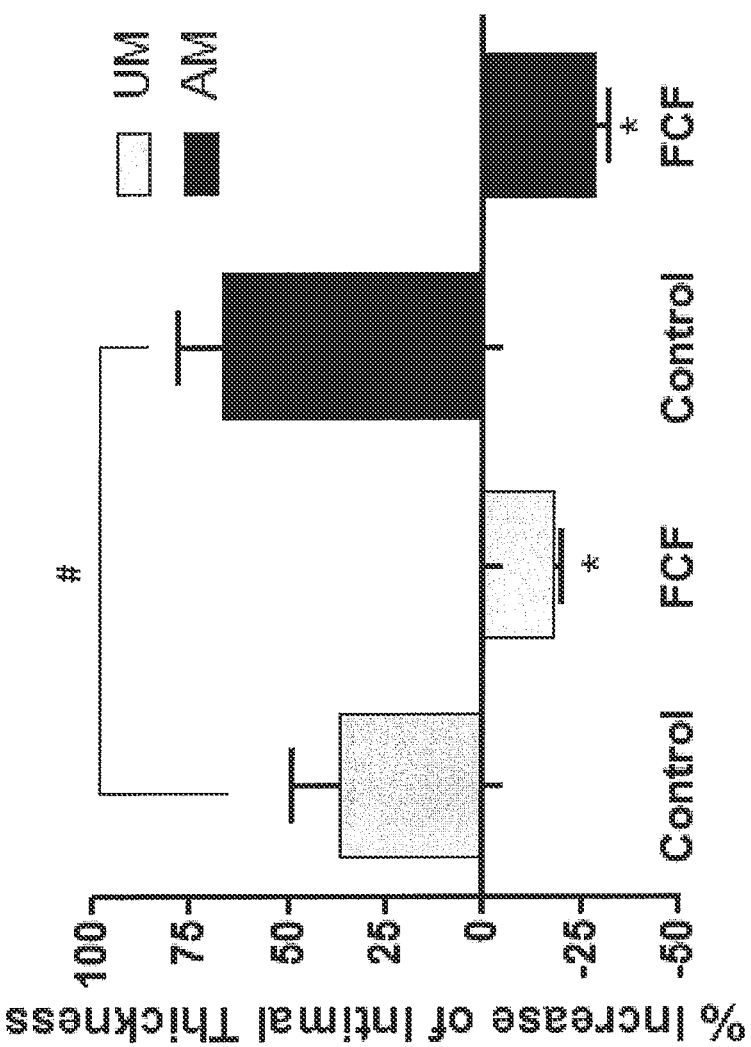
FIG. 13 demonstrates that the erioglaucine reduces intimal thickness in human saphenous vein in an organ culture model.

Segments of human saphenous vein were collected prior to preparation of the vein for transplantation into the arterial circulation (unmanipulated, UM) and after surgical preparation (after manipulation, AM) from the same patients in PlasmaLyte and were used within 2 hr of harvest. The segment was cut into ~1 mm rings and one ring from each group was fixed in formalin (Pre-culture). The other rings were cultured in RPMI medium supplemented with 1% L-glutamine, 1% penicillin/streptomycin and 30% fetal bovine serum at 5% $CO_2$ and 37° C. in the absence (Control) or presence of 50 µM erioglaucine (FCF) for 14 days. After 14 days, the rings were fixed in formalin, sectioned at 5 µm and stained using Verhoff Van Gieson stain. Light micrograph of the rings was captured using an Axiovert 200 and intimal thickness was measured using AxioVision. Data represent % increase of intimal thickness related to basal intimal thickness of the pre-culture ring which was set as 0%. The error bars show the standard error of the mean. Manipulation during vein preparation increased the thickening of the intimal layer (#p=0.053 in paired t-test) and treatment with erioglaucine significantly (*p<0.05) inhibited the development of intimal thickness when compared to Control (FIG. 13).

Figure 14:
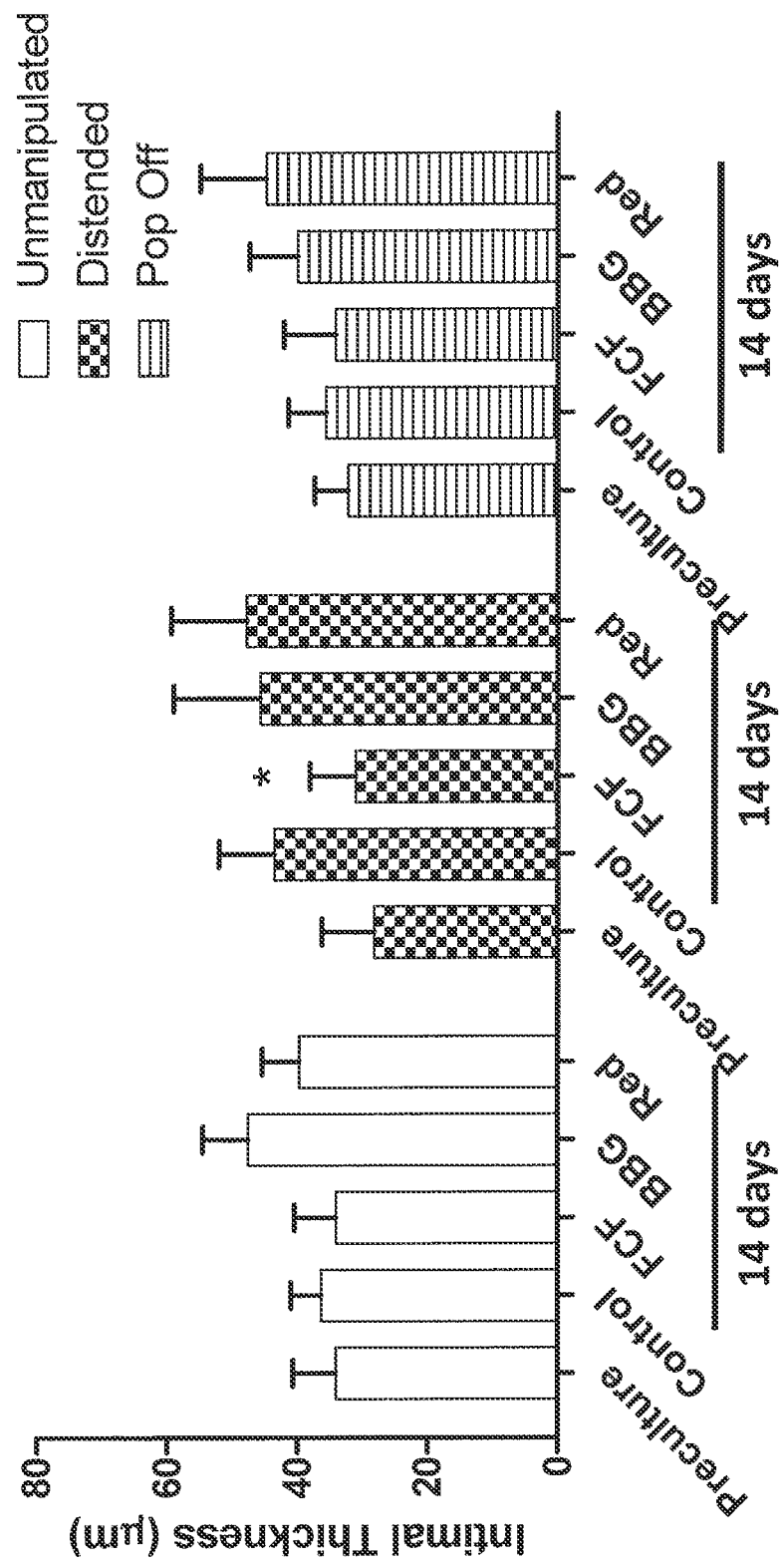
FIG. 14 shows erioglaucine reduces intimal layer thickening in distended porcine saphenous vein.

Fresh porcine saphenous vein was harvested by a no touch method under sterile conditions and stored in cold transplant harvest buffer (100 mM potassium lactobionate, 25 mM $KH_2PO_4$, 5 mM $MgSO_4$, 30 mM Raffinose, 5 mM Adenosine, 3 mM Glutathione, 1 mM Allopurinol, 50 g/L Hydroxyethyl starch, pH 7.4). The vessels were used within 24 hr of harvest. The veins were divided into three segments that were left untreated (Unmanipulated, n=7), distended (Distended, n=8) to >300 mm Hg, or distended in the presence of the pressure relief valve (Pop Off, n=7). Each segment was then cut into ~1 mm rings and one ring from each condition was immediately fixed in formalin (Pre-culture). The other rings were cultured in RPMI medium supplemented with 1% L-glutamine, penicillin/streptomycin and 30% Fetal bovine serum at 5% $CO_2$ and 37° C. in the absence (Control) or presence of either 50 µM erioglaucine (FCF), 50 µM brilliant blue G (BBG) or 50 µM Allura Red (Red) for 14 days. After 14 days, the rings were fixed in formalin, sectioned at 5 µm and stained using Verhoff Van Gieson stain. Light micrograph of the rings was captured using a Axiovert 200 and intimal thickness was measured using AxioVision. Treatment with erioglaucine but not allura red inhibited distension induced increases in intimal thickening, *p<0.05 compared to Distended-Control (FIG. 14).

Figure 15:
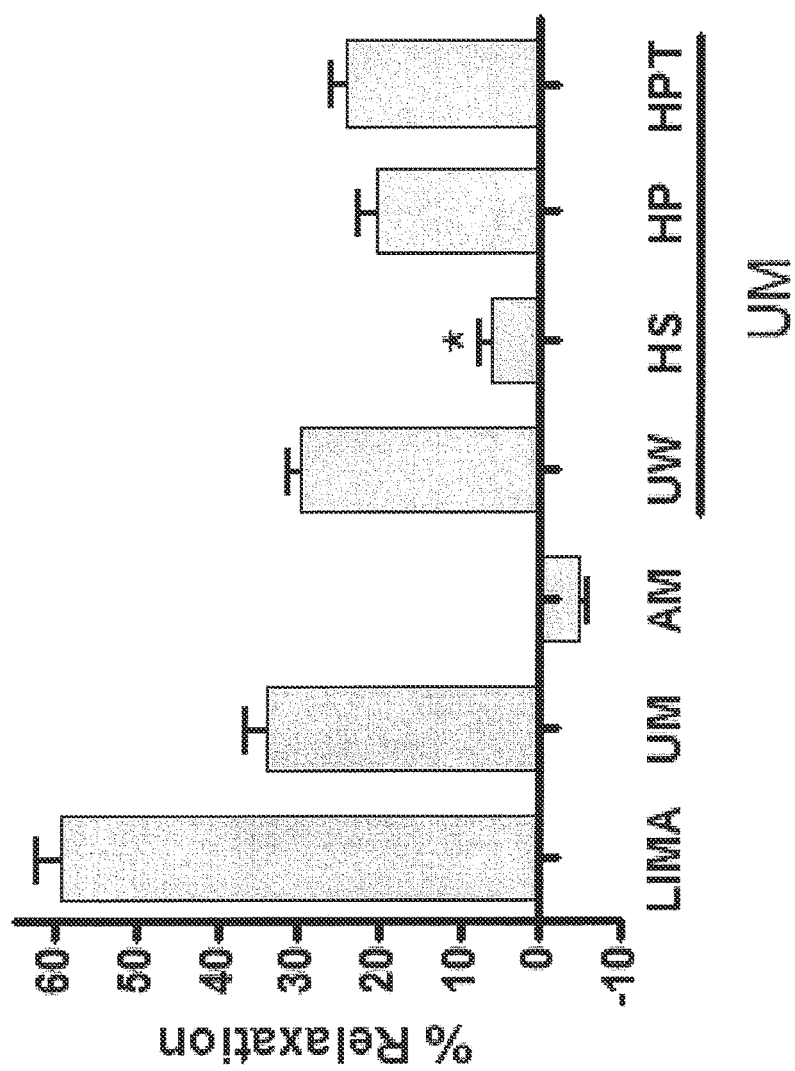
FIG. 15 demonstrates that manipulation during surgical preparation impair endothelial dependent relaxation in human saphenous vein.

Rings of human left internal mammary artery (LIMA; n=3) and saphenous veins were obtained prior to preparation of the vein for transplantation into the arterial circulation (unmanipulated, UM; n=5) and after surgical preparation (after manipulation, AM; n=5). Rings cut from the UM segments were incubated in University of Wisconsin Solution (UW), heparinized saline (HS), heparinized PlasmaLyte (HP) or heparinized PlasmaLyte containing 30 mM trehalose (HPT) for 2 hrs at room temperature. Rings were cut from the veins, suspended in a muscle bath and equilibrated in bicarbonate buffer. The rings were pre-contracted with $10^{-6}$ M phenylephrine and then treated with $5\times10^{-7}$ M carbachol to determine endothelial dependent relaxation. Rings from the LIMA had greater endothelial dependent relaxation than saphenous vein (FIG. 15). Manipulation during surgical preparation led to decreased endothelial dependent relaxation (FIG. 15). Storage in heparinized saline [*p<0.05 compared to HS for all UM groups (UM, UW, HP, & HPT)], but not in heparinized plasmalyte, heparinized plasmalyte plus trehalose or transplant harvest solution led to decreased endothelial dependent relaxation (FIG. 15). Data is presented as % relaxation (compared to the maximal phenylephrine induced contraction).

Figure 16:
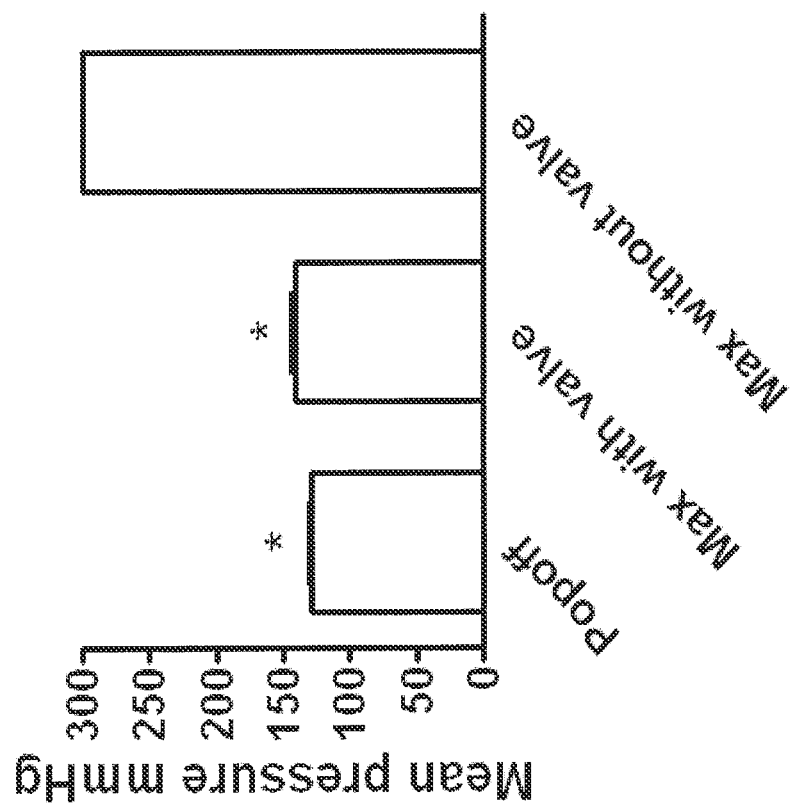
FIG. 16 shows that a pressure release (pop-off) valve limits pressure in human saphenous vein during manual distention.

De-identified discarded segments of human saphenous vein (n=5) were collected, after informed consent approved by the Institutional Review Board of the Vanderbilt University (Nashville, Tenn.), from patients undergoing coronary artery bypass or peripheral vascular bypass surgery. The veins were stored in a saline solution until the end of the surgical procedure at which time they were placed in cold transplant harvest buffer (100 mM potassium lactobionate, 25 mM $KH_2PO_4$, 5 mM $MgSO_4$, 30 mM raffinose, 5 mM adenosine, 3 mM glutathione, 1 mM allopurinol, 50 g/L hydroxyethyl starch, pH 7.4). The vessels were tested within 24 hours of harvest and storage in transplant harvest buffer at 4° C. A pop off valve was connected to a syringe at one end and to a cannulated saphenous vein at the other. The distal end of the saphenous vein was also cannulated and connected to a pressure transducer. Pressure was monitored while the vein was distended with a hand held syringe with and without the pressure release valve. The pressure monitor would not measure pressures above 300 mmHg. This created three groups and they were the following: pop-off pressure (Popoff), max pressure with pop-off valve (Max with valve), and max pressure without pop-off valve (Max without valve). The veins that had a pop-off valve had a mean pressure of 129±1.265 mm Hg and maximum pressure of 141.8±1.985 mm Hg, while the veins with out the pop off valve had a maximum pressure of 300±0.00 mm Hg (FIG. 16). The average and maximum pressure in the veins with the pop-off valve were significantly different from the veins without the pop-off valve (p≤0.05).

Fresh porcine saphenous vein was harvested by a no touch method under sterile conditions and stored in cold transplant harvest buffer (100 mM potassium lactobionate, 25 mM $KH_2PO_4$, 5 mM $MgSO_4$, 30 mM Raffinose, 5 mM Adenosine, 3 mM Glutathione, 1 mM Allopurinol, 50 g/L Hydroxyethyl starch, pH 7.4). The vessels were used within 24 h of harvest. Veins (n=4) were manually distended with a syringe in the absence (Distended) or presence of an in line pressure release valve (pop-off). Control segments were not distended (ND). After distension, rings were cut from the segments and suspended in a muscle bath. The rings were precontracted with $10^{-6}$ M phenylephrine and then treated with $5 \times 10^{-7}$ M carbachol to determine endothelial dependent relaxation. Data is presented as the % relaxation (compared to the maximal phenylephrine induced contraction). Manual distension with a hand held syringe led to significant decreases (p<0.0005) in endothelial dependent relaxation and the pressure release valve prevents this loss of endothelial dependent relaxation (FIG. 17).

Porcine coronary arteries were freshly isolated from euthanized pigs and placed directly into cold transplant harvest buffer (100 mM potassium lactobionate, 25 mM $KH_2PO_4$, 5 mM $MgSO_4$, 30 mM Raffinose, 5 mM Adenosine, 3 mM Glutathione, 1 mM Allopurinol, 50 g/L Hydroxyethyl starch, pH 7.4). Coronary arteries were dissected free of fat and adventitial tissues and the endothelium was removed. Transverse rings (1.0 mm thickness) were cut and suspended in muscle bath, via silk 3-0 linked to force transducers (Kent Scientific, Conn.) interfaced with a Data Translation A-D board (Data Translation, MA). Data was acquired with the Power Lab software program. Porcine coronary artery rings were suspended in a muscle bath and equilibrated in Krebs Ringer bicarbonate buffer for 2 h. The rings were stretched and the length progressively adjusted until maximal tension was obtained. The rings were contracted with 110 mM KCl (with equimolar replacement of NaCl in bicarbonate buffer), and the force generated was measured and converted to stress [Newtons $(N)/m^2$]=force (g)×0.0987/area, where area is equal to the wet weight [mg/length (mm at maximal length)] divided by 1.055. Rings were washed and equilibrated for another 30 mins. Rings were treated with 5 μM histamine, 110 mM KCl, 1 mM papaverine (PAP), 1 mM papaverine for 10 min followed by 5 μM histamine or 1 mM papaverine for 10 min followed by 110 mM KCl and force generated was measured- and converted to stress. Representative force tracings of rings treated with 5 μM histamine (Hist), 110 mM KCl (KCl), 1 mM papaverine (PAP), 1 mM papaverine for 10 min followed by 5 μM histamine (Pap+Hist) or 1 mM papaverine for 10 min followed by 110 mM KCl (Pap+KCl) were depicted in FIG. 18A. Decrease in stress was converted to a percentage of the maximal initial KCl contraction which was set as 100%. Papaverine treatment reduced basal tension in the rings (−15.0±3.135%) (FIG. 18B). Pretreatment of rings with papaverine completely inhibited histamine (−12.0±4.163 compared to 98.613±11.049) and KCl (−20.0±10.00 compared to 103.33±2.404%) induced contraction (FIG. 18B).

De-identified discarded segments of human saphenous vein (n=6) were collected, after informed consent approved by the Institutional Review Board of the Vanderbilt University (Nashville, Tenn.), from patients undergoing coronary artery bypass or peripheral vascular bypass surgery. The veins were stored in a saline solution until the end of the surgical procedure at which time they were placed in cold transplant harvest buffer (100 mM potassium lactobionate, 25 mM $KH_2PO_4$, 5 mM $MgSO_4$, 30 mM raffinose, 5 mM adenosine, 3 mM glutathione, 1 mM allopurinol, 50 g/L hydroxyethyl starch, pH 7.4). The vessels were tested within 24 hrs of harvest and storage in transplant harvest buffer at 4° C. Veins were cleaned off fat and adventitial tissues and the endothelium was removed. Transverse rings (1.0 mm thickness) were cut and suspended in muscle bath, via silk 3-0 linked to force transducers (Kent Scientific, Conn.) interfaced with Powerlab data acquisition system and Chart software (AD Instruments, Colorado Springs, Colo.). Human saphenous vein rings were suspended in a muscle bath and equilibrated in Krebs Ringer bicarbonate buffer for 2 hr. The rings were stretched and the length progressively adjusted until maximal tension was obtained. The rings were contracted with 110 mM KCl (with equimolar replacement of NaCl in bicarbonate buffer), and the force generated was measured and converted to stress [Newtons $(N)/m^2$]=force (g)×0.0987/area, where area is equal to the wet weight [mg/length (mm at maximal length)] divided by 1.055. Rings were washed and equilibrated for another 30 mins. Rings were treated with 0.5 μM norepinephrine (NE), 1 mM papaverine (Pap), or 1 mM papaverine for 10 min followed by 0.5 μM NE and force generated was measured and converted to stress. Decrease in stress was converted to a percentage of the maximal initial KCl contraction which was set as 100%. Representative force tracings of rings treated with 0.5 μM NE (NE), 1 mM papaverine (Pap), or 1 mM papaverine for 10 min followed by 0.5 μM NE were depicted in FIG. 19A. Decrease in stress was converted to a percentage of the maximal initial KCl contraction which was set as 100%. n=6. Papaverine treatment reduced basal tension in the rings (−9.772.0±3.226%). Pretreatment of human saphenous vein with papaverine completely inhibited NE (−3.210±5.119 compared to 89.935±18.344%) induced contraction (FIG. 19B).

Figure 20:
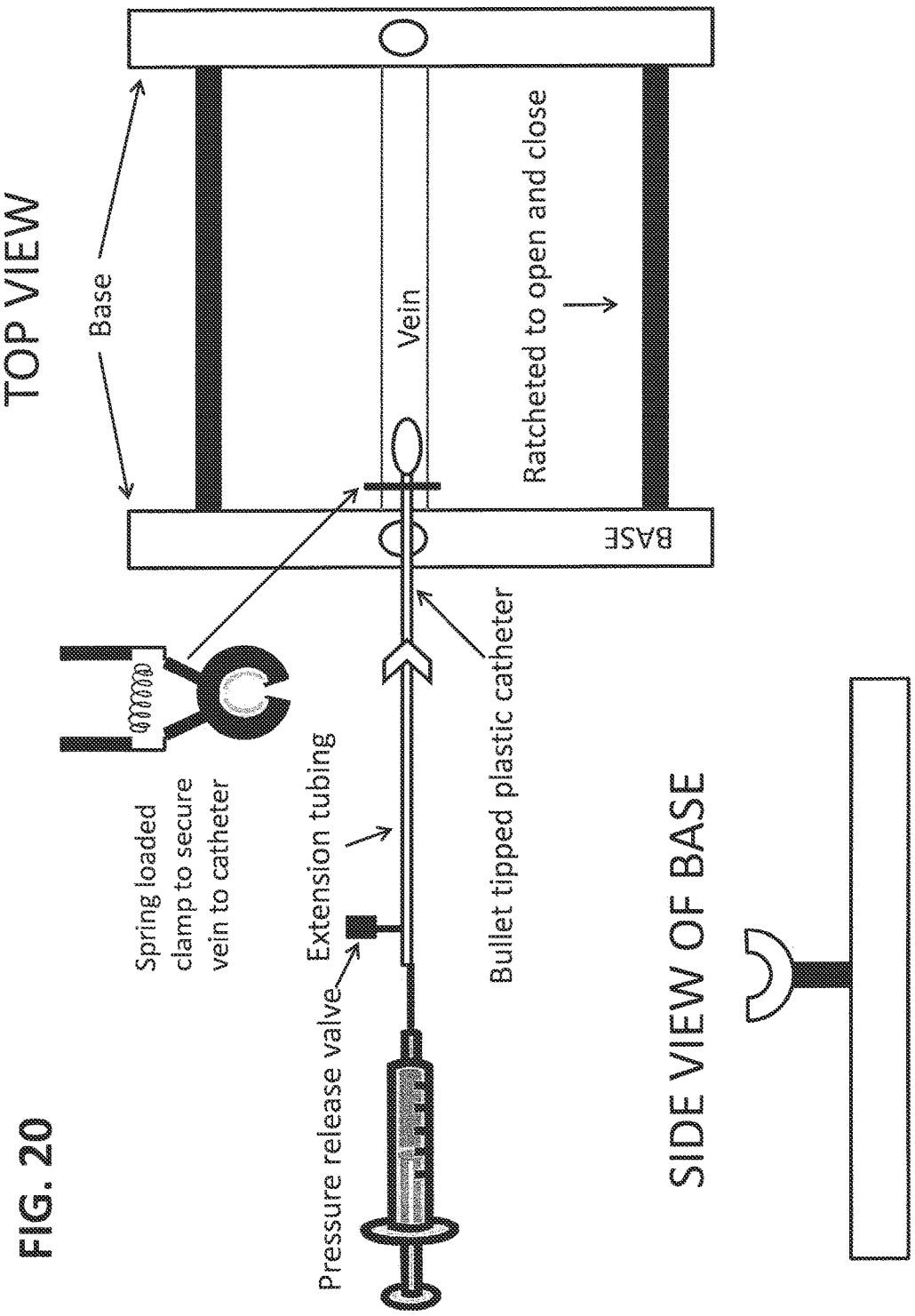
FIG. 20 shows the vein harvest device kit.

Vein harvest device is shown in FIG. 20. The distal end of the vein (the vein is reversed because of valves in the vein) is cannulated with a bullet tipped plastic catheter which has a lumen for irrigation and secured to the catheter with a spring loaded clamp. The catheter is clipped into the base. An additional bullet tipped catheter with no lumen is attached to the proximal end of the vein clipped into the opposite end of the base. The device is ratcheted open until the vein is at the same length as in vivo. A syringe with extension tubing and an in line pressure release valve is attached to the distal end of the vein. The vein can now be distended and side branches ligated.

Example 4—Prophetic Clinical Protocol

The greater saphenous vein will be surgically harvested using standard surgical technique. The distal end of the vein will be cannulated with a bullet tipped vein cannula and secured with either a clamp or a silk tie. The pressure release valve will be attached to the cannula with a 10 or 20 cc syringe attached to the other end of the valve. In some cases, extension tubing will be placed between the syringe and the valve. The vein will be distended with the vein harvest solution and tributaries identified and ligated with either silk ties or clips. The vein will be marked with the marker in the kit along one long surface to maintain orientation of the vein. In some cases, the vein may be marked prior to removal from the patient. The vein will then be placed in the harvest solution until implanted into the arterial circulation. In one embodiment, the dye from the pen will contain a $P2X_7$ receptor antagonist, and the harvest solution will not contain a $P2X_7$ receptor antagonist. In another embodiment, the dye from the pen will not contain a $P2X_7$ receptor antagonist, but the solution will. In a third embodiment, both the pen dye and the solution will contain a $P2X_7$ receptor antagonist.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

VII. REFERENCES

The following references, to the extent that they provide exemplary procedural or other details supplementary to those set forth herein, are specifically incorporated herein by reference.

Motwani J G, Topol E J (1998) Aortocoronary saphenous vein graft disease: pathogenesis, predisposition, and prevention. Circulation 97: 916-931.

Clowes A W, Reidy M A (1991) Prevention of stenosis after vascular reconstruction: pharmacologic control of intimal hyperplasia—a review. J Vasc Surg 13: 885-891.

Allaire E, Clowes A W (1997) Endothelial cell injury in cardiovascular surgery: the intimal hyperplastic response. Ann Thorac Surg 63: 582-591.

Mosse P R, Campbell G R, Wang Z L, Campbell J H (1985) Smooth muscle phenotypic expression in human carotid arteries. I. Comparison of cells from diffuse intimal thickenings adjacent to atheromatous plaques with those of the media. Lab Invest 53: 556-562.

LoGerfo F W, Quist W C, Cantelmo N L, Haudenschild C C (1983) Integrity of vein grafts as a function of initial intimal and medial preservation. Circulation 68: 11117-124.

Kent K C, Liu B (2004) Intimal hyperplasia—still here after all these years! Ann Vasc Surg 18: 135-137.

Mann M J, Whittemore A D, Donaldson M C, Belkin M, Conte M S, et al. (1999) Ex-vivo gene therapy of human vascular bypass grafts with E2F decoy: the PREVENT single-centre, randomised, controlled trial. Lancet 354: 1493-1498.

Alexander J H, Hafley G, Harrington R A, Peterson E D, Ferguson T B, Jr., et al. (2005) Efficacy and safety of edifoligide, an E2F transcription factor decoy, for prevention of vein graft failure following coronary artery bypass graft surgery: PREVENT IV: a randomized controlled trial. Jama 294: 2446-2454.

Dashwood M R, Loesch A (2007) Surgical damage of the saphenous vein and graft patency. J Thorac Cardiovasc Surg 133: 274-275.

Dashwood M, Anand R, Loesch A, Souza D (2004) Surgical Trauma and Vein Graft Failure: Further Evidence for a Role of ET-1 in Graft Occlusion. J Cardiovasc Pharmacol 44: S16-S19.

Furchgott, R. F. and J. V. Zawadzki, The obligatory role of endothelial cells in the relaxation of arterial smooth muscle by acetylcholine. *Nature,* 1980. 288: p. 373-376.

Khakh, B. S., and North, R. A. (2006) P2X receptors as cell-surface ATP sensors in health and disease. *Nature* 442, 527-532.

Cario-Toumaniantz, C., Loirand, G., Ladoux, A., and Pacaud, P. (1998) P2X7 receptor activation-induced contraction and lysis in human saphenous vein smooth muscle. *Circ Res* 83, 196-203.

Donnelly-Roberts, D. L., Namovic, M. T., Faltynek, C. R., and Jarvis, M. F. (2004) Mitogen-activated protein kinase and caspase signaling pathways are required for P2X7 receptor (P2X7R)-induced pore formation in human THP-1 cells. *J Pharmacol Exp Ther* 308, 1053-1061.

Monahan et al., *FASEB* 23:557-564, 2009.

Pfeiffer, Z. A., Aga, M., Prabhu, U., Watters, J. J., Hall, D. J., and Bertics, P. J. (2004) The nucleotide receptor P2X7 mediates actin reorganization and membrane blebbing in RAW 264.7 macrophages via p38 MAP kinase and Rho. *J Leukoc Riot* 75, 1173-1182.

Peng, W., Cotrina, M. L., Han, X., Yu, H., Bekar, L., Blum, L., Takano, T., Tian, G. F., Goldman, S. A., and Nedergaard, M. (2009) Systemic administration of an antagonist of the ATP-sensitive receptor $P2X_7$ improves recovery after spinal cord injury. *Proc Natl Acad Sci USA* 106, 12489-12493.

Seal & Panitch, *Biomacromolecules* 4(6): 1572-82 (2003).
PCT/US2007/16246
PCT/US2008/72525
Alcaraz et al., *Bioorganic & Medicinal Chemistry Letters* 13(22): 4043-4046 (2003)
Carroll et al., *Purinergic Signalling* 5(1): 63-73 (2009)
U.S. Pat. No. 7,709,469
U.S. Pat. No. 6,812,226
U.S. Pat. No. 7,741,493
U.S. Pat. No. 7,718,693
U.S. Pat. No. 7,326,792
U.S. Patent Publication 2010/0292295
U.S. Patent Publication 2010/0292224
U.S. Patent Publication 2010/0286390
U.S. Patent Publication 2010/0210705
U.S. Patent Publication 2010/0168171
U.S. Patent Publication 2010/0160389
U.S. Patent Publication 2010/0160388
U.S. Patent Publication 2010/0160387
U.S. Patent Publication 2010/0160384
U.S. Patent Publication 2010/0160373
U.S. Patent Publication 2010/0144829
U.S. Patent Publication 2010/0144727
U.S. Patent Publication 2010/0105068
U.S. Patent Publication 2010/0075968
U.S. Patent Publication 2010/0056595
U.S. Patent Publication 2010/0036101
U.S. Patent Publication 2009/0264501
U.S. Patent Publication 2009/0215727
U.S. Patent Publication 2009/0197928
U.S. Patent Publication 2009/0149524
U.S. Patent Publication 2009/0005330
U.S. Patent Publication 2008/0132550
U.S. Patent Publication 2008/0009541
U.S. Patent Publication 2007/0122849
U.S. Patent Publication 2007/0082930
U.S. Patent Publication 2005/0054013
U.S. Patent Publication 2005/0026916
U.S. Patent Publication 2002/0182646

What is claimed is:

1. A vein transplant kit comprising:
 (a) a $P2X_7$ receptor antagonist;
 (b) a physiologic buffered solution or reagents for making such; and
 (c) a tissue marking pen.

2. The kit of claim 1, further comprising a container suitable for bathing a vein explant.

3. The kit of claim 1, further comprising one or more of heparin, an anti-contractile agent, an anti-oxidant agent, an oligosaccharide, a colloid agent, an anti-inflammatory agent, an endothelial function preservative, a metabolic regulator, a hydrogel, an inhibitor of a heat shock protein, magnesium sulfate, and/or an inhibitor of MAPKAP kinase 2.

4. The kit of claim 1, wherein said physiologic buffered solution comprises phosphate buffered saline, MOPS, Hepes, Pipes, acetate or Plasmalyte.

5. The kit of claim 1, wherein said physiologic buffered solution is pH 7.0-7.6.

6. The kit of claim 1, wherein said $P2X_7$ receptor antagonist comprises erioglaucine/Blue Dye #1 or brilliant blue G.

7. The kit of claim 1, further comprising a clamp designed to hold said vein explant.

8. The kit of claim 3, wherein said anti-contractile agent is a phosphodiesterase inhibitor, a calcium channel blocker, a nitric oxide donor, or a cyclic nucleotide analog.

9. The kit of claim 3, wherein said anti-oxidant agent is N-acetylcysteine, allopurinol, glutathione, mannitol, ascorbic acid, a tocopherol, a tocotrienol or a green tea phenol.

10. The kit of claim 3, wherein said oligosaccharide is lactobionic acid, raffinose, or trehalose.

11. The kit of claim 3, wherein said colloid agent is hydroxyethyl starch, dextran, blood or albumin.

12. The kit of claim 3, wherein said anti-inflammatory agent is a corticosteroid, a nonsteroidal anti-inflammatory, a mapkap kinase 2 inhibitor, anti-TNF-$\alpha$, anti-IL-1-$\beta$, or a Cox-2 inhibitor.

13. The kit of claim 3, wherein said endothelial function preservative is an angiotensin converting enzyme inhibitor, an angiotensin receptor inhibitor, a statin, metformin or an estrogen.

14. The kit of claim 3, wherein said metabolic regulator is glucose, adenosine amylin, calcitonin related gene peptide, or insulin.

15. The kit of claim 3, wherein said hydrogel is composed of a natural polysaccharide such as alginate, dextran, chitosan, and glycosaminoglycan, or a hydrophilic polymer such as polyethylene glycol, methylcellulose, hydroxymethylcellulose, hydroxyethylcellulose, polyhydroxbuterate, or poly (n-isopropylacrylamide).

16. The kit of claim 3, wherein said inhibitor of a heat shock protein is an inhibitor of HSP27, such as an siRNA or miRNA that inhibits HSP27 expression.

17. The kit of claim 3, wherein said inhibitor of MAPKAP kinase 2 is a peptide inhibitor.

18. The kit of claim 5, wherein said pH is 7.35-7.45.

19. The kit of claim 5, wherein said pH is 7.0, 7.1, 7.2, 7.3, 7.4, 7.5 or 7.6.

20. The kit of claim 3, wherein said $P2X_7$ receptor antagonist is disposed in said tissue marking pen.

21. The kit of claim 3, wherein said $P2X_7$ receptor antagonist is disposed in said physiologic buffered solution.

22. The kit of claim 3, wherein said tissue marking pen is empty.

* * * * *